US00RE35233E

United States Patent [19]

Smith et al.

[11] E Patent Number: Re. 35,233

[45] Reissued Date of Patent: * May 7, 1996

[54] METHOD OF TREATING CATABOLIC DYSFUNCTION

[75] Inventors: Robert J. Smith; Douglas W. Wilmore, both of Brookline, Mass.

[73] Assignee: Brigham and Women's Hospital, Boston, Mass.

[ * ] Notice: The portion of the term of this patent subsequent to Aug. 15, 2006, has been disclaimed.

[21] Appl. No.: 180,780

[22] Filed: Jan. 10, 1994

Related U.S. Patent Documents

Reissue of:

[64] Patent No.: 5,039,704
Issued: Aug. 13, 1991
Appl. No.: 261,649
Filed: Oct. 24, 1988

U.S. Applications:

[60] Continuation of Ser. No. 851,282, Mar. 4, 1992, abandoned, which is a division of Ser. No. 906,530, Sep. 12, 1986, Pat. No. 4,857,655, which is a continuation-in-part of Ser. No. 775,214, Sep. 12, 1985, abandoned.

[51] Int. Cl.[6] ..... A61K 31/195

[52] U.S. Cl. ..... 514/563

[58] Field of Search ..... 514/563

[56] References Cited

U.S. PATENT DOCUMENTS

| | | | |
|---|---|---|---|
| 1,909,591 | 5/1933 | Nevin | 167/55 |
| 2,283,817 | 5/1942 | Martin et al. | 167/55 |
| 2,662,046 | 12/1953 | Howe et al. | 167/58 |
| 2,868,693 | 1/1959 | Shive et al. | 167/55 |
| 3,195,778 | 7/1965 | Coates et al. | 222/80 |
| 3,217,711 | 11/1965 | Pecina et al. | 128/214 |
| 3,574,857 | 4/1971 | Cevallos et al. | 424/319 |
| 3,701,666 | 10/1972 | Wimitz et al. | 99/1 |
| 3,793,450 | 2/1974 | Schnell et al. | 424/195 |
| 3,832,465 | 8/1974 | Ghadimi et al. | 424/177 |
| 3,920,838 | 11/1975 | Flatt et al. | 424/319 |
| 3,950,529 | 4/1976 | Fischer et al. | 514/400 |
| 3,982,534 | 9/1976 | Buckman | 128/214 |
| 3,988,466 | 10/1976 | Takagi et al. | 424/274 |
| 4,200,095 | 4/1980 | Reti | 128/214 |
| 4,265,240 | 5/1981 | Jenkins | 128/214 |
| 4,334,535 | 6/1982 | Wilson et al. | 128/214 |
| 4,396,383 | 8/1983 | Hart | 604/56 |
| 4,857,555 | 8/1989 | Smith et al. | 514/563 |

FOREIGN PATENT DOCUMENTS

| | | | |
|---|---|---|---|
| 1285491 | 7/1991 | Canada | 167/261 |
| 0059694 | 9/1982 | European Pat. Off. | 5/14 |
| 0087750 | 9/1983 | European Pat. Off. . | |
| 3206784 | 2/1982 | Germany | 37/18 |
| 59-27822 | 2/1984 | Japan . | |

OTHER PUBLICATIONS

Milakofsky, L., et al., *Life Sci.* 36:753–761 (1985).
Roth, E., et al., *Bio. Abs.* 72:Abstr. 25963 (1980).
Clowes, G. H., et al., *Surgery* 88:531–543 (1980).
Ohta, H., et al., *Neuropharmacology* 24:445–451 (1985).
Schwartau, M., et al., *Z. Ernaehrungswiss* 23:206–218 (1984).
Derr, R. F., et al., *Bio. Abs.* 72:Abstr. 47176 (1981).
Schrek, R., et al., *J. Natl. Cancer Inst.* 51:1103–1107 (1973).
Zanello, M. E., et al., *Bio. Abs.* 70:Abstr. 52747 (1980).
Bergner, H., et al., *Bio. Abs.* 79:Abstr. 88557 (1985).
Okabe, S., et al., *Digestion* 14:325–331 (1976).
Harada et al., *Folia Pharmacol. JPN* 69:322(P) (1976); see also *Bio. Abs.* 11:24358 (1973).
Heath, D. F., et al., *Biochem. J.* 125:765–771 (1971).
Albers, S., et al., *Chem. Abs.* 102:Abstr. 23355h (1985).
Elia, M., et al., *Chem. Abs.* 103:Abstr. 102688t (1985).
Moyer, M. P., et al., *Chem. Abs.* 104:Abstr. 219523x (1986).
Viallard, V., et al., *Bio. Abs.* 104:Abstr. 127504p (1986).
Tischler, M. E., et al., *Bio. Abs.* 71:Abstr. 14875 (1980).
Hong, C. Z., et al., *Bio. Abs.* 78:Abstr. 70581 (1984).
Crawford, J., et al., *Bio. Reviews* 31:29511 (1986).
Smith, R. J., et al., *Clinical Research* 34:393A (1986).
Longton, R. W., et al., *Bio. Reviews* 10:24019 (1973).
Durschlag, R. P., et al., *Am. J. Physiol.* 248:C422–C448 (1985).
Newsholme, E. A., et al., *Bioscience Reports* 5:393–400 (1985).
Cersosimo, P. E., et al., *Amer. J. Physiol.* 250:E622–E628 (1986).
Hambleton, P., et al., *Brit. J. Exp. Path.* 61:208–216 (1980).
Chipponi, J. X., et al., *Amer. J. of Clinical Nutrition* 35:1112–1116 (1982).
Physicians Desk Reference—1972—pp. 705–707.
Physicians Desk Reference—1983—pp. 1418–1421.
Physicians Desk Reference—1987—pp. 1419–1422.
Roth, E., et al., *Bio. Abs.* 80:Abst. 96470 (1985).
Ivanova, I. A., et al., *Bio. Abs.* 80:Abstr. 34601 (1985).
Roth, E., et al., *Bio. Abs.* 80:Abstr. 96352 (1985).
Smith, R. J., et al., *J. Cellular Physiol.* 120:197–203 (1984).
Aoki, T. T., et al., *J. Clin. Invest.* 68:1522–1528 (1981).
Smith, R. J., et al., *Diabetes* 31:P24A (1982).
Durschlag, R. P., et al., *J. Fed. Proced.* 42:996 (1983).
Smith, R. J., et al., *Diabetes* 33:Suppl., 2A (1984).
Souba, W. W., et al., *Metabolism* 34:450–456 (1985).
Furst, P., et al., *Acta Chirugica Scand.*, suppl. 494:136–138 (1979).
Hanson, P. J., et al., *Biochem. J.* 166:509–519 (1977).
Korein, J., *N.E.J. Medicine* 301:1066 (1979).
Korein, J., *Neurology* 27:899–900 (1977).

(List continued on next page.)

*Primary Examiner*—Raymond Henley, III
*Assistant Examiner*—K. Weddington
*Attorney, Agent, or Firm*—Sterne, Kessler, Goldstein & Fox

[57] ABSTRACT

The invention relates to a method of treating a catabolic dysfunction in an animal, which comprises administering to an animal a therapeutically effective amount of glutamine, or an analog thereof.

10 Claims, 11 Drawing Sheets

OTHER PUBLICATIONS

Kapadia, C. R., et al., *J. Parenteral Enteral Nutrition* 9:583–589 (1985).
Souba, W. W., et al., *J. Parenteral Enteral Nutrition* 9:18–22 (1985).
Amberger, I., et al., *Hoppe–Seyler's Z, Physiol. Chem.* 364:1253–1254 (1983).
Mulbacher, F. et al., *Amer. J. Physiol.* 247:E75–E83 (1984).
Souba, W. W., et al., *Surgical Forum* 34:74–78 (1983).
Souba, W. W., et al., *Archives of Surgery* 120:66–70 (1985).
Kapadia, C. R., et al., *Surgical Forum* 33:19–21 (1982).
Souba, W. W., Thesis in Harvard Medical Library, Jun. 1984.
Askanazi, J., et al., *Annals of Surgery* 192:78–85 (1980).
Askanazi, J. et al., *Annals of Surgery* 191:465–472 (1980).
Derr, R. et al., *Nutrition Reports International* 23(4):749–753 (1981).
Johnson, D. et al., *Ann. Surg.* 204(5):513–523 (1986).
Johnson, D. et al., *Current Surgery* 43:31–34 (1986).
Ohta, H. et al., *Chem. Abstr.* 103:81, Abstr. 32689t (1985).
Okabe, S. et al., *Digestive Diseases* 20(7):626–631 (1975).
Okabe, S. et al., *Japan J. Pharmacol.* 24:169–171 (1974).
Schrek, R. et al., *Bio. Abs.* 57(4):2220, Abstr. 21213 (1973).
Schwartua, M. et al., *Biol. Abstr.* 79(7):AB–680–681, Abstr. 61030 (1985).
Smith, R. et al., *Intracellular Protein Catabolism,* Khairallah et al. (eds.), Alan R. Liss, N.Y. pp. 633–635 (1985).
Souba, W. et al., *Surgery* 94 (2):342–350 (1983).
Albers, S. et al., *Akt. Ernahr.* 9:147–149 (1984).
Clowes, G. et al., *Biol. Abstr.* 71(6):4101, Abstr. 39209 (1981).
Baskerville, A. et al., *British J. Exp. Path.* 61:132–138 (1980).

• SALINE
○ FREAMINE
□ GLUTAMINE ALONE
△ FREAMINE PLUS GLUTAMINE

METHOD OF TREATING CATABOLIC DYSFUNCTION

Matter enclosed in heavy brackets [ ] appears in the original patent but forms no part of this reissue specification; matter printed in italics indicates the additions made by reissue.

This invention was funded by research grants from the National Institutes of Health, Trauma Center Grant No. GM29327-05, and the United States Department of the Army, Contract No. DAMD-17-81-C-1201, which provide to the United States Government certain rights in the invention.

CROSS REFERENCE TO RELATED APPLICATION

This application *is a continuation of application Ser. No. 07/851,282, filed Mar. 4, 1992; now abandoned, which* is a division of U.S. application Ser. No. 906,530 filed Sep. 12, 1986 now U.S. Pat. No. 4,857,655 which is a continuation-in-part of application Ser. No. 775,214, filed Sep. 12, 1985, now abandoned.

BACKGROUND OF THE INVENTION

1. Field of the Invention

The present invention relates to a method for treating or preventing tissue damage in an animal afflicted with a catabolic dysfunction.

2. Description of the Prior Art

Catabolic dysfunctions are those physiological conditions in which the degradation of an anatomical structure occurs. Anatomical structures commonly affected in this manner are skeletal muscle and the lining of the gut. Often such catabolic activity occurs following surgery, sepsis, burn injury, cancer chemotherapy, radiation therapy/injury, glucocorticoid therapy or, often, inadequate food intake. Such catabolic dysfunctions are a major cause of death and disability and are characterized by abnormal glutamine metabolism.

Glutamine is a non-essential amino acid which can be synthesized by most tissues. Unlike most amino acids, glutamine has two amine moieties: an alpha-amino group and an amide group. It is the presence of the amide group which enables glutamine to remove ammonia from the peripheral tissues of the body and transport nitrogen to visceral organs. In addition, it is common for tissues that remove glutamine from the circulation to utilize the carbon skeleton for energy.

Glutaminase and glutamine synthetase are the two principal enzymes involved in the regulation of glutamine metabolism. Glutaminase catalyzes the hydrolysis of glutamine to glutamate and ammonia, while glutamine synthetase catalyzes the synthesis of glutamine from glutamate and ammonia. While most tissues have both of these enzymes, usually one is more active than the other, depending on the particular tissue.

Glutamine synthesis and exportation occurs primarily in skeletal muscle and the brain. In turn, glutamine is consumed by such replicating cells as fibroblasts, lymphocytes, tumor cells and intestinal epithelial cells. Characteristically, these cells possess high levels of glutaminase activity and low levels of intracellular glutamine. This fact may also be clinically significant for patients having large wounds, inflammation associated with infection, or a gastrointestinal dysfunction which precludes normal enteral feeding since, in these cell types, the desirable proliferation of cells in these conditions may depend on the availability of sufficient levels of glutamine.

In the gastrointestinal tract, glutamine is used as a respiratory fuel. The enteral administration of glutamine results in increased uptake of luminal glutamine by the gut mucosa accompanied by a simultaneous decrease in uptake of glutamine from the circulation. Thus, the consumption of glutamine by the gut is balanced between these two sources of glutamine.

Most of the glutamine taken up by the gastrointestinal tract occurs via the epithelial cells lining the villi of the small intestine. The glutamine metabolism which occurs in the small intestine provides a major source of energy for the gut and produces precursors for hepatic ureagenesis and gluconeogenesis by processing nitrogen and carbon from other tissues.

Evidence of the essential role of glutamine in the maintenance of normal intestinal structure and function was suggested in a study by Baskerville et al., British Journal of Experimental Pathology, 61: 132 (1980). These authors lowered the concentration of plasma glutamine to undetectable levels by infusing purified glutaminase into rhesus monkeys, marmosets, rabbits, and mice. As a result of this treatment, these animals displayed vomiting, diarrhea, villus atrophy, mucosal ulcerations, and intestinal necrosis.

Martin et al. (U.S. Pat. No. 2,283,817) disclose a composition containing glutamine which is used as a detoxicant, rather than a dietary supplement. In the patent, glutamine is combined synergistically with other amino acids to act directly on a toxin to inhibit any deleterious effect.

In Shive et al. (U.S. Pat. No. 2,868,693), the patentees disclose glutamine-containing compositions for the treatment of peptic ulcers.

Further evidence of the potential protective effect of glutamine was shown by Okabe et al., Digestive Disease, 20: 66 (1975), who found that glutamine could protect against aspirin-induced gastric ulcerations in humans.

This visceral glutamine requirement may be even greater during critical illness, when glutamine metabolism by the small intestine is known to be increased (Souba et al., Surgery, 94(2): 342 (1983)).

At present, the nutritional requirements of patients who are unable to feed themselves adequately are met through the administration of enteral or parenteral diets. Enteral diets are usually administered using small-bore tubing which is placed through the nose into the gastric, or duodenal regions, or through surgical implantation as in, for example, gastrostomy, or jejunostomy. Those enteral formulas which are presently available can be divided into four basic categories: elemental, polymeric, modular, and altered amino acids. These formulae contain glutamine. The levels of nutrients present in the enteral diets, however, are generally based upon the dietary requirements of a normal individual and not that of a patient suffering from a catabolic disease.

Elemental formulas require minimal digestive action and are composed primarily of small peptides and/or amino acids, glucose oligosaccharides, and vegetable oil or medium-chain triglycerides.

In polymeric formulas, complex nutrients such as, for example, soy protein, lactalbumin, or casein are utilized as a source of protein; maltodextrins, or corn syrup solids as a source of carbohydrate; and vegetable oils, or milk fat as a source of fat.

Modular diets can be produced by combining protein, carbohydrate, or fat with a monomeric or polymeric formula to meet special nutritional requirements.

Formulas which are composed of altered amino acid compositions are used primarily for patients with genetic errors of nitrogen metabolism or acquired disorders of nitrogen accumulation, the object here being to limit the intake by the patient of certain amino acids which may be detrimental.

Parenteral diets are usually administered intravenously. These intravenous fluids are sterile solutions composed of simple chemicals such as, for example, sugars, amino acids, and electrolytes, which can be easily assimilated.

The term "total parenteral nutrition" (TPN) is used to describe formulas for use in patients who derive their entire dietary requirements intravenously. Total parenteral nutrition formulas, unlike enteral formulas, do not normally contain glutamine. The absence of glutamine from parenteral formulas is due, in part, to concern with respect to its instability at room temperature, and the resulting generation of ammonia and pyroglutamic acid. There has also been concern about the generation of glutamic acid from glutamine because of the potential toxicity of glutamic acid as a neurotransmitter. In fact, these concerns do not appear to be justified. At a pH just below neutrality, glutamine degrades very slowly (Souba, S.C.D. Thesis in Harvard Medical School Library, June, 1984).

Total parenteral nutrition results in villus atrophy, a phenomenon which is generally reversible when oral feedings are resumed. Since TPN formulas lack glutamine, the body's requirements for this amino acid must be derived from synthetic pathways in body tissues.

In patients with critical illnesses, net protein catabolism is associated with markedly diminished muscle glutamine pools (Askanazi et al. Annals of Surgery, 191: 465 (1980); Askanazi et al., Annals of Surgery, 191: 465 (1980)), reduced plasma levels of glutamine (Askanazi et al., Annals of Surgery, 192: 78 (1980); Askanazi et al., Annals of Surgery, 191: 465 (1980)), and a presumed increase in intestinal glutamine utilization (Souba et al., Archives of Surgery, 120: 66 (1985); Souba et al., Surgery, 94(2): 342 (1983)). Glucocorticoids are known to increase glutamine consumption by the small intestine (Souba et al., Surgical Forum, 34: 74 (1983)).

None of the prior art studies have shown that the breakdown of skeletal muscle, the atrophy of intestinal villi, or other catabolic dysfunctions, which occur during total parenteral nutrition, can be prevented through the administration of high levels of glutamine.

SUMMARY OF THE INVENTION

In the invention, an animal having, or at risk of having, a catabolic dysfunction is given a therapeutically effective amount of glutamine. This amount of glutamine is greater than that normally encountered in the diet of healthy individuals. This increased level of glutamine is necessary to compensate for the greater demand for glutamine which occurs during certain catabolic dysfunctions. In the absence of exogenous glutamine during these catabolic dysfunctions, glutamine would be derived through the breakdown of muscle tissue. The decline in glutamine concentrations in the plasma in spite of accelerated glutamine release from muscle during catabolic dysfunctions indicates systemic glutamine deficiency. In spite of accelerated glutamine release from muscle, intestinal mucosal cell demand exceeds the supply. This, in turn, predisposes to intestinal villus atrophy.

Thus, the present invention provides a method of treating catabolic dysfunctions in an animal which comprises administering to the animal a therapeutically effective amount of glutamine or functional analogues thereof.

Provision of exogenous glutamine to a stressed patient may better support the metabolic requirements of the small intestine and possibly decrease the rate of systemic protein catabolism. Provision of glutamine in patients with inflammatory bowel disease may also be beneficial.

It is conceivable that the therapeutic efficacy of glucocorticoids in inflammatory bowel disease is related not only to their anti-inflammatory properties, but also to their role in increasing substrate metabolism within the enterocytes lining the gut. Administration of exogenous glutamine may provide even more substrate for the enterocytes and may also prevent glutamine depletion of plasma and skeletal muscle. Similarly, glutamine may promote the survival of transplanted small bowel or support gut metabolism in infants with intestinal immaturity.

BRIEF DESCRIPTION OF THE PREFERRED EMBODIMENTS

Figure 1:
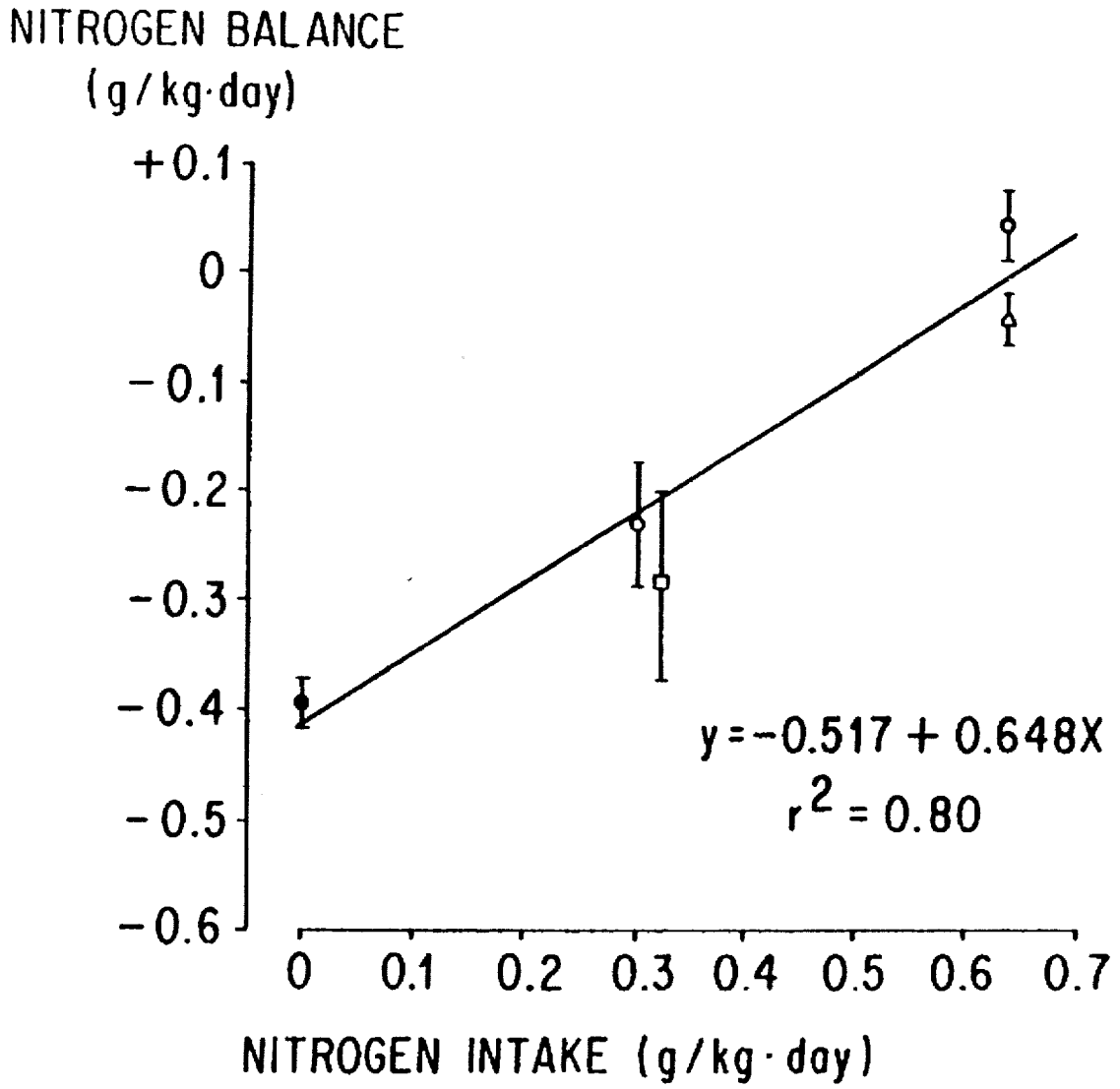
FIG. 1 shows a plot of nitrogen balance as a function of nitrogen intake.

The inventors have devised a new method of treating catabolic dysfunctions. The present invention comprises the administration to an animal afflicted with, or likely to develop, a catabolic dysfunction, a therapeutically effective amount of glutamine or a functional analogue thereof. This therapeutically effective amount is greater than that present in a normal diet. The normal dietary intake for humans is about 2 to 4 g/day.

A catabolic dysfunction is a condition which induces a catabolic biochemical pathway in which the degradation of an anatomical structure occurs. The dietary administration of glutamine appears to satisfy the bio-chemical requirements of these catabolic conditions such that it is not necessary for the body to synthesize glutamine or to obtain glutamine from the breakdown of skeletal muscle.

The present invention is intended to be used in all catabolic dysfunctions where there is an increased demand for glutamine. These catabolic dysfunctions can be either enteral or parenteral. For example, the atrophy of the villi of the small intestine which occurs when TPN diets are administered is an enteral catabolic dysfunction. Atrophy of the villi does not usually occur due to direct catabolic activity on the enterocytes, but rather, is due to the lack of glutamine in the diet of patients on a parenteral diet.

Parenteral catabolic dysfunctions which display increased demand for glutamine occur during or following surgery, sepsis, burn injuries, anorexia, and uncontrolled diabetes.

Animals in which the invention is effective are those commonly classified as mammals, including humans.

The term "enteral" is intended to indicate that portion of the alimentary canal between the stomach and the anus.

The term "parenteral" denotes that region outside of the digestive tract.

The term "substantially associated with" as applied to the catabolic dysfunctions for which the method of the invention is effective, means those wherein the bio-chemical demand for glutamine occurs during or after the catabolic dysfunction, and is related thereto.

The administration of glutamine can be by both enteral and parenteral means.

An example of how the enteral administration of glutamine is accomplished is by using small-bore tubing placed via the nose into the gastric or duodenal regions, or through surgical implantation as in, for example, gastrostomy, or jejunostomy.

Examples of parenteral routes of administration include, but are not limited to, such routes as subcutaneous, intramuscular, or intravenous injection, nasopharyngeal or mucosal absorption, or transdermal absorption. In most cases, the glutamine is administered intravenously. In intravenous administration, the therapeutically effective amount of glutamine is in a liquid form which is administered from a reservoir directly via the placement of a needle into a large vein of the patient, wherein the needle is connected to the reservoir by tubing.

Regardless of which route of administration is utilized, the glutamine can be administered either singly or as a dietary supplement. When used as a dietary supplement, the glutamine can be mixed with an existing enteral or parenteral diet prior to administration to the patient. It is also possible to administer the glutamine without mixing it directly with the other components of a diet as, for example, in intravenous feeding wherein the glutamine is not directly added to the main intravenous bottle, but instead is added to a common reservoir using a "piggy-back" bottle.

Functional analogues, derivatives, substitution products, isomers, or homologues of glutamine which retain the characteristics of glutamine are contemplated as equivalents. Preferred are those analogues capable of donating an amine group and being metabolized in the Krebs cycle. Most preferred are compounds which possess the amino acid residue at one terminus of a carbon chain and an amine moiety at the other terminus of the carbon chain.

The therapeutically effective dose ranges for the administration of glutamine are those large enough to prevent the catabolism or atrophy of the tissues of the body in order to maintain metabolic homeostasis. In an enteral diet glutamine would be administered at a rate greater than or equal to 0.3 grams per kilogram of body weight per day. Such administration rates could be 0.3 to 2.0 grams per kilogram of body weight per day, preferably 0.3 to 1.5 grams per kilogram of body weight per day, and more preferably 0.4 to 1.0 grams per kilogram of body weight per day. The rate of administration for glutamine when administered intravenously would be greater than or equal to 0.1 grams per kilogram of body weight per day. Such administration rates could be 0.2 to 3.0 grams per kilogram of body weight per day, preferably 0.3 to 2.5 grams per kilogram of body weight per day, more preferably 0.4 to 2.0 grams per kilogram of body weight per day.

According to the method of the invention, glutamine may be administered by simply modifying existing dietary formulas to contain the proper concentration of glutamine. Most preferably, the glutamine would remain in a dry form such as, for example, a sterile lyophilized powder which is aseptically hydrated at the time of administration and mixed at the proper concentration with the other components of the dietary composition. Alternatively, the glutamine could be premixed with the other components of a dry formula which is aseptically rehydrated at time of administration, or stored as a frozen concentrate which is thawed and mixed at the proper concentration at time of use.

The use of glutamine by the method according to the invention is ideally suited for the preparation of compositions. These compositions may comprise glutamine alone or in combination with other chemicals. These other chemicals can be pharmaceutically accept able carriers, as well as other active substances of the diet as, for example, free amino acids, protein hydrolysates, or oils.

Preparations for parenteral administration include sterile aqueous or non-aqueous solutions, suspensions, and emulsions. Carriers or occlusive dressings can be used to increase skin permeability and enhance absorption.

The invention also relates to a medicament or pharmaceutical composition comprising the components of the invention, the medicament being used for inhibiting catabolic dysfunctions.

The invention also relates to glutamine-rich compositions for preventing or ameliorating catabolic dysfunctions. Compositions which are glutamine-rich contain glutamine in levels which are therapeutically effective and are greater than that present in the normal diet.

Containers containing the composition of the invention can be used to facilitate the administration of glutamine according to the method of the invention. These containers are designed to contain, for example, the daily dosage of glutamine to be administered to the patient.

Containers adapted for intravenous administration of glutamine alone or in combination with other amino acids are especially useful. Such containers could comprise a receptacle for the liquid glutamine- containing composition, and a liquid conducive means capable of attachment to a needle.

The liquid conducive means could be any object capable of conveying the liquid composition in the receptacle to the needle such as, for example, plastic tubing.

The needle attached to the conducive means could either be inserted directly into a blood vessel of the human recipient or could be inserted into a reservoir to enable mixing with another solution before being administered to the patient.

The above disclosure generally describes the present invention. A more complete understanding can be obtained by reference to the following specific examples which are provided herein for purposes of illustration only and are not intended to be limiting unless otherwise specified.

EXAMPLE 1

Animal Care and Operative Procedure

Twenty-two mongrel doges, weighing between 20 and 40 kg, were obtained from a farm where they had been regularly exercised and screened for parasites. All female animals were nonpregnant. While in the kennel, the animals were maintained in accordance with the guidelines of the Committee on Animals at Harvard Medical School and the Committee on Care and Use of Laboratory Animals of the Institute for Laboratory Animal Resources, the National Research Council (DHEW Publication #NIH 78-23, reviewed 1978). The animals were kept in individual kennels at a constant temperature of 20° C., with 24-hour high exposure. They were exercised for two hours every morning, provided water ad libitum, and given a single daily feeding between 1:00 and 3:00 pm of Agway Respond 2000 Dry Dog Chow ® (contains at least 25% protein, 10% fat, and the remaining calories as carbohydrate). Five to seven days were allowed for the dogs to acclimate to the kennel conditions, during which time they were trained to rest quietly in a Pavlov stand. On the day before obtaining basal samples, all food was removed from the kennel at 5:00 pm. After an overnight fast, the dog was walked for at least 20 minutes, placed in a Pavlov stand, and foreleg vein was cannulated. After the dog had rested in the stand for at least 20 minutes, a venous blood sample was obtained for amino acid determination. Following rapid induction of anesthesia with intravenous sodium thiopental (Abbott Laboratories, 5 mg/kg body weight), a biopsy of the vastus lateralis muscle was obtained by the method of Bergstrom et al., Journal of Applied Physiology, 36: 693–697 (1974). The animal was then taken out of the stand and a 5-ml sample of arterial blood was obtained from the femoral artery via percutaneous puncture.

The animal was allowed to recover from the biopsy for a minimum of two days prior to the standard operative procedure. On the day prior to surgery, all food was again removed from the kennel at 5:00 pm. At 7:00 am, the dog was walked for 20 minutes and then taken to the operating suite where it was anesthetized with intravenous sodium pentobarbital (Abbott Laboratories, 30 mg/kg body weight). An endotracheal tube was placed, and the animal was allowed to spontaneously breathe a mixture of oxygen and room air. The dog was placed on an operating table in a supine position, and a cannula was placed by percutaneous puncture into the external jugular vein and directed into the superior vena cava. After noting the starting time, the infusion solution was administered via this cannula by constant infusion (IMED pump ®, San Diego, Calif.) at 4 ml/hr/kg. Penicillin G (E. R. Squibb, Princeton, N.J.; 600 mg) and Keflin ® Eli Lilly, Indianapolis, Ind.; 1 gram) were given intravenously. The urinary bladder was catheterized, the initial urine sample was discarded, and the catheter was connected to a closed urine bag for 24-hour collection. The abdomen and flanks of the dog were shaved, and the skin was washed with soap and water and prepared with a povidone iodine prep solution (Clinipad Corporation, Guilford, Conn.). The dog was draped with sterile sheets and the abdominal cavity entered via a vertical infra-umbilical incision in females and a right paramedial incision in males. The bowel was retracted into the upper abdomen, and the exposed retroperitoneum incised. The right deep circumflex iliac artery and vein and the medial sacral artery were isolated by sharp and blunt dissection. A specially prepared catheter consisting of a 6 cm segment of polyethylene tubing (2.08 mm OD) coated with silastic and linked to a 2.8 mm OD polyethylene catheter was inserted 6 cm cranially into the aorta via a right deep circumflex iliac artery. A similar catheter was inserted into the middle sacral artery, its tip being positioned approximately 1 cm proximal to the bifurcation of the aorta, but distal to the inferior mesenteric artery. A third catheter was inserted into the inferior vena cava via the right deep circumflex iliac vein and positioned distal to the renal vein. All catheters were secured and exteriorized through stab wounds in the flank. The abdomen was then closed and the animal turned onto its left side. The exterior catheters were cut to appropriate lengths, plugged with blunt needles connected to intermittent injection ports (Jelco ®, Critikon, Inc., Tampa, Fla.), flushed with saline, filled with heparin (1,000 units/ml), and buried subcutaneously. The injection ports were positioned high on the flank of the animal under the skin and in the approximate vicinity of the vertebral column. This allowed access to the aorta and vena cava by percutaneous puncture of the injection ports of the catheters. Two further doses of Keflin ® (1 gram) were given 8 and 24 hours post-operatively via the venous catheter.

Following the operative procedure, the animal was placed on its side, and body temperature was maintained with heat lamps and blankets during recovery from anesthesia. Approximately five hours after the start of the infusion, the animal was placed in a Pavlov stand, and a solution of para-aminohippuric acid (PAH, 0.5% w/v in saline) was infused at a rate of 0.76 ml/minute with a Harvard pump into the distal aorta through the medial sacral artery catheter. After 40 minutes of dye infusion, simultaneous arterial and venous samples were obtained for measurement of amino acid and PAH concentrations. Three sample sets were drawn at 10-minute intervals over a period of 20 minutes. The catheters were then flushed, filled with heparin, and the animal was kept in a Pavlov sling. Twenty-three hours following the initiation of the experiment, the hindquarter flux studies were repeated. After 24 hours, the urine collection was terminated. The animal received intravenous sodium thiopental, as previously described, and biopsy of the vastus lateralis muscle in the leg not previously biopsied was performed. The intravenous infusion was terminated, and the animal placed in a metabolic cage for the ensuing 24 hours where it was offered water ad libitum and no food.

EXAMPLES 2

Infusion Solutions

All animals received an infusion at a rate of 4 ml/hr/kg. Five control animals received 0.9% saline. Other animals were given commercially available amino acid solution (FreAmine III®, American McGaw) at two different concentrations designed to deliver approximately 0.312 (N=2) or 0.624 (N=6) grams of nitrogen/24 hr/kg body weight. The higher dose was designed to provide the equivalent of 4 grams of protein/24 hr/kg body weight. Three animals received a solution containing glutamine at 0.312 grams nitrogen/24 hr/kg. A final group (N=6) received an equal mixture of glutamine and FreAmine®, providing nitrogen at 0.624 grams/24 hr/kg. The glutamine solutions were made by dissolving L-glutamine (Sigma, St. Louis, Mo.) in distilled water to form a 0.157 M solution which was then adjusted to pH 6.8 with sodium hydroxide. This solution was sterilized by filtration through a 0.22 uM membrane and stored at 4° C. for less than 24 hours. On the morning of utilization, the solutions were formulated at required concentrations in 2-liter bags (American McGaw) and maintained at 4° C. until use. A 10 ml sample was taken from each bag at the end of the infusion and stored at −20° C. for analysis of nitrogen content. An additional 10 ml sample was adjusted to pH 4.75 as described below and stored frozen for analysis of glutamine content.

EXAMPLE 3

Preparation and Analysis of Samples

Whole blood and plasma samples were deproteinized by combining with equal volumes of ice cold 10% (w/v) perchloric acid and then centrifuging at 3,000 rpm at 4° C. for 20 minutes. A 2 ml aliquot of the supernatant was buffered with 0.2 ml of 0.2M sodium acetate buffer (pH 4.90), adjusted to pH 4.75–4.90 with 5N potassium hydroxide, and brought to a final volume of 4 ml with distilled water. The samples were stored at −20° C. for later batch analysis of glutamine and glutamate concentrations, using an enzymatic microfluorometric assay modified from the method of Lund, "L-glutamine Determination with Glutaminase and Glutamate Dehydrogenase," in Methods of Enzymatic Analysis, Vol. 4, Bergmeyer (ed), Academic Press, New York, 1974, pp. 1719–1722.

During the muscle biopsy procedure, a stop watch was started immediately when the tissue was removed. The muscle was dissected free of fat and connective tissue and divided into two unequal portions. Both samples were weighed at least four times over the ensuing two minutes, and the weight and time following biopsy were recorded. Actual muscle wet weight at time zero was calculated from the best fit linear regression of weight plotted against time. The smaller sample (approximately 15 mg) was dried to a constant weight in a 90o oven, and the weight of dry, fat-free solids was obtained after extraction in petroleum ether. This sample was then digested in 250 ul of 1N nitric acid, and the chloride content was measured by titration with silver nitrate using a semi-automated titrator (Radiometer, Copenhagen). Plasma chloride was also determined and intra- and extracellular water calculated by the method of Bergstrom et al., supra. The second muscle sample (approximately 100 mg) was homogenized in 0.5 ml of ice cold perchloric acid (10% w/v) with a Polytron Homogenizer (Brinkman, Westbury, N.Y.). The homogenate was centrifuged and the supernatant prepared for enzymatic glutamine and glutamate analysis.

At the start of this study, plasma and intracellular glutamine and glutamate concentrations were determined by an enzymatic method previously described (Muhlbacher et al., American Journal of Physiology, 247: E75-E83 (1984)). Concentrations of other amino acids were determined by automated high performance liquid chromatography (HPLC) after pre-column derivatization with o-phthalaldehyde. All amino acids commonly found in proteins were quantitated except glutamine, glutamate, proline, cysteine, and lysine. As the study progressed, techniques were developed for glutamine-glutamate measurement using HPLC. Samples measured by the two techniques (enzymatic and HPLC) yielded comparable glutamine-glutamate concentrations; hence, only HPLC analysis was utilized in the latter portion of the study. The concentration of PAH in the arterial and venous samples was determined spectro photometrically following deproteinization with 5% trichloroacetic acid (Muhlbacher et al., supra).

Urine excreted during the 24 hours of infusion was collected in the closed urinary collecting system and stored in acidified, refrigerated containers. Aliquots were stored frozen at −20° C. for batch analysis. The nitrogen content of the infusion solution and urine was determined in the same batch by the macro-Kjeldahl method (Peters et al., Quantitative Clinical Chemistry, Vol. II, Williams & Wilkins, Baltimore, Md., 1932, pp. 516–538).

Statistical calculations were performed on an IBM 4341 Computer utilizing a standard statistical package (Minitab, The Pennsylvania State University, State College, Pa., 1983). The results are expressed as mean ±SEM. Paired and unpaired Student's t-tests were used as appropriate. Analysis of variance was used for multiple group comparisons. Regression analysis was performed using methods of least squares. Because of the small sample size in the groups receiving 0.312 grams of nitrogen/24 hr/kg, most statistical comparisons were only performed between the other groups.

Hindquarter blood flow was calculated as previously described (Muhlbacher et al., supra), and the rate was expressed per kg body weight to account for variation in size of the animals. Amino acid flux rates were calculated s the product of blood flow and arterial-venous concentration differences. Three sets of samples were drawn, flux was calculated for each set, and the mean of the three values determined (Muhlbacher et al., supra). Total amino acid nitrogen in whole blood, plasma, and intracellular water was calculated by taking into account the nitrogen content of each amino acid and summing the individual concentrations.

EXAMPLE 4

Plasma and Intracellular Amino Acid Concentrations

Plasma amino acid concentrations were measured preoperatively and 24 hours following the standard operation. In the saline-treated animals, the total nitrogen content of the plasma was unchanged by the operative procedure (Table I). The glutamine concentration remained constant, but the branched chain amino acids rose, the sum of their concentrations increasing from 326±21 to 501±9 umol/l ($p<0.01$). In the animals receiving 0.624 grams N/24 hr/kg, there was an upward trend in the plasma nitrogen concentration that was statistically significant only in the group receiving the mixture of amino acids plus glutamine. The plasma glutamine concentration also rose in this group. Branched chain amino acids were elevated in all animals receiving amino acid infusions.

Skeletal muscle nitrogen concentration declined during saline infusion (Table 11). This decrease in total amino acid nitrogen was reflected primarily by a fall in glutamine from 21.48±3.21 umol/l intracellular water to 15.86±3.80 ($p<0.05$). Although the sum of the concentrations of nonessential amino acids diminished, the sum of total essential amino acids in the intracellular pool remained unchanged. No change in intracellular nitrogen or glutamine occurred in animals receiving 0.624 gm of amino acid nitrogen/24 hr/kg (Table II). There was an upward trend in the intracellular concentration of branched chain amino acids with infusion of the higher amino acid loads, although statistical significance was achieved only in the animals receiving the mixture of amino acids and glutamine. There was not a significant change in the total concentrations of essential and non-essential amino acids in these two groups following operation. In contrast to the animals receiving the higher dose of nitrogen, the five animals infused with 0.312 gm N/24 hr/kg did not consistently maintain the skeletal muscle intracellular nitrogen pool, regardless of the solution infused. Intracellular glutamine fell in three of the animals, remained unchanged in one, and increased in one (data not shown).

Thus, providing amino acid at 0.624 gm N/24 hr/kg as an amino acid mixture with or without glutamine, maintained the skeletal muscle intracellular amino acid pool. A decrease in the intracellular pool, which was characterized by a fall in intracellular glutamine, occurred consistently in the animals receiving saline and was variable in the animals receiving the lower dose of amino acids.

Net hindquarter amino acid flux, calculated as the sum of the nitrogen flux of the individual amino acids, averaged −19.05±4.06 umol N/min/kg when measured at 6 hours post-operation in the animals receiving saline. This was significantly greater than the efflux rates of −7.70±5.9 and −6.50±1.18 umol N/min/kg observed in the two groups of animals receiving 0.624 gm of amino acids/24 hr/kg (Table III). However, glutamine efflux from the hindquarter was unchanged among these three groups. In contrast, branched chain amino acids were released in the dogs receiving only saline, but taken up in both groups of animals receiving the higher doses of amino acids. Hindquarter exchange of branched chain amino acids appeared to be related to the rate of branched chain amino acid administration; the hindquarter demonstrated branched chain amino acid release in the saline-treated group, balance with the solution containing amino acids plus glutamine, and greater uptake in the group receiving the highest branched chain amino acid dose. In the five animals receiving 0.312 gm N/24 hr/kg, there was not a significant alteration in hindquarter nitrogen efflux compared to the salinetreated dogs. However, there was considerable variation in these flux data, and the number of animals studied was small. Hindquarter amino acid flux studies 24 hours following operation demonstrated no differences between groups (Table III).

Nitrogen excretion in the five animals infused with saline was 0.492±0.022 gm N/24 hr/kg. In the six animals receiving the highest dose of commercial amino acid mixture, measured nitrogen intake was 0.632±0.001 gm N/24 hr/kg, and nitrogen excretion averaged 0.684±0.031 (Table IV). In the six animals receiving the solution made up of one-half commercial amino acid solution and one-half glutamine, nitrogen intake was comparable, but excretion was greater, averaging 0.775±0.019 gm N/24 hr/kg ($p<0.05$). Nitrogen balance in these two groups was significantly less negative than in the animals receiving saline, averaging −0.052±0.031 and −0.140±0.022 gm N/24 hr/kg, respectively. In the five animals that received approximately 0.312 gm N/24 hr/k9, the average nitrogen excretion was intermediate between that observed in the saline controls and in the animals receiving the larger quantity of infused nitrogen. Taken together, these studies demonstrated that nitrogen balance approached equilibrium as the quantity of administered nitrogen increased (FIG. 1). When glutamine was combined with a commercial glutamine-free amino acid solution, the effects on nitrogen balance were additive. When summed together, the nitrogen retained in response to the infusion of commercial amino acids or glutamine alone accounted for the nitrogen retained when the solutions were combined.

These studies show that operative stress in dogs stimulates net skeletal muscle protein breakdown, as evidenced by negative nitrogen balance and increased amino acid efflux from the hindquarter in association with a fall in the intracellular skeletal muscle free amino acid pool. Previous studies have demonstrated that protein wasting is not related to fasting or anesthesia, but is clearly a response to the operative stress (Kapadia et al., Surgical Forum, 33: 19±21 (1982)). The release of amino acids from the hindquarter 6 hours post.-operation in the saline-treated group was approximately 6 to 8 times that observed in chronically-catheterized, post-absorptive dogs studied under basal conditions (Muhlbacher et al., American Journal of Physiology, 247:E75– E83(1984)). This rate of hindquarter nitrogen release cannot be accounted for by depletion of the intracellular free amino acid pool and therefore must reflect net skeletal muscle proteolysis.

Provision of amino acids in the perioperative period offset the nitrogen loss, maintained or increased plasma amino acid concentrations, and diminished the fall in the skeletal muscle intracellular free amino acid pool. These effects appear to be related to the quantity of amino acid nitrogen infused. Whole body and hindquarter nitrogen losses were greatly decreased at the highest amino acid doses, which also maintained intracellular pools of glutamine and other amino acids. These results differ from the findings reported by Askanazi et al., Annals of Surgery, 191: 465 (1980), who described a decline in the intracellular concentrations of glutamine and other amino acids in patients after hip replacement that could not be reversed by infusion of dextrose and amino acids. Results obtained using the method of the invention indicate that this earlier finding may be related to the quantity of amino acids infused and/or the lack of glutamine in the infusate. Infusion of lower concentrations of amino acids (0.312 gm N/24 hr/kg), either as glutamine alone or as FreAmine®, failed to maintain the intracellular amino acid pool in three of the five animals studied. In contrast, the higher rate of amino acid infusion stabilized or increased the intracellular pool. Thus, it appears that an adequate quantity of administered nitrogen can maintain the skeletal muscle intracellular amino acid pool post-operatively.

The change in the intracellular free amino acid pool in saline-infused animals, largely attributable to a rapid fall in glutamine, was prevented when adequate nitrogen was provided. This occurred even when glutamine was not present in the commercially available solution. The mechanism by which intracellular glutamine was maintained under these circumstances is unclear, although it seems probable that glutamine substrate for glutamine synthesis was derived from the branched chain amino acids via transamination. For unexplained reasons, net glutamine efflux was similar in all groups. Hindquarter release of glutamine was not accelerated by branched chain amino acids or attenuated by the provision of glutamine in the amino acid solution. The results in this post-operative model differ from reported effects of branched chain amino acids in normal humans, in whom branched chain amino acid forearm uptake following the administration of leucine orally was associated with accelerated glutamine release (Aoki et al., Journal of Clinical Investigation, 65: 1522 (1981)).

Although there were marked differences in composition of the two amino acid solutions administered at the rate of 0.624 gm N/24 hr/kg, hindquarter nitrogen efflux was comparable in both groups of animals. This occurred even though the quantity of essential amino acids and branched chain amino acids in the balanced solution was twice that in the glutamine-containing solution. Thus, in this experimental model of operative stress, glutamine supplementation of a balanced amino acid formula was at least as effective as two-fold concentration of standard balanced formula in diminishing hindquarter loss.

In the dogs that received saline, branched chain amino acids were released from skeletal muscle. Quantitative transfer rates calculated from these data suggest that a marked uptake of branched chain amino acids must have occurred in visceral organs, most probably in the liver, during the early post-operative period. The provision of branched chain amino acids appeared to offset this translocation, perhaps by both meeting visceral requirements and reversing skeletal muscle efflux. A quantitative relationship also existed between hindquarter nitrogen balance and preservation of the intracellular nitrogen pool. When intracellular pools were maintained, the hindquarter was near nitrogen equilibrium; when saline was administered, amino acid concentrations in the intracellular pools were markedly depleted and there was a marked loss of hindquarter nitrogen. Although the relationship between skeletal muscle proteolysis and nitrogen concentration in the free amino acid pool is unknown, these data suggest that skeletal muscle nitrogen balance is related to the intracellular amino acid concentration and that glutamine can play an essential role in maintaining a homeostatic balance in the body.

TABLE I

| | Plasma Amino Acid Concentration (Mean ± SEM) | | | | | |
|---|---|---|---|---|---|---|
| | Pre-operative | | | 24 Hours Post-operative | | |
| Solution Infused | Total Nitrogen (mmol/l) | GLN*** Conc (umol/l) | Sum BCAA Conc (umol/l) | Total Nitrogen (mmol/l) | GLN*** Conc (umol/l) | Sum BCAA Conc (umol/l) |
| Saline | 4.51 ± 0.37 | 845 ± 99 | 326 ± 21 | 4.56 ± 0.29 | 742 ± 60 | 501 ± 9* |
| Amino Acids (0.624 gm N/24 hr/kg) | 4.84 ± 0.58 | 829 ± 87 | 339 ± 31 | 5.57 ± 0.61 | 631 ± 75 | 767 ± 99** |
| Amino Acids + Glutamine (0.624 gm N/24 hr/kg) | 3.96 ± 0.29 | 643 ± 36 | 297 ± 31 | 5.92 ± 0.49* | 1042 ± 88* | 592 ± 82* |

*p < 0.01, when compared to pre-operative value by paired t-test.
**p < 0.001, when compared to pre-operative value by paired t-test.
***GLN = glutamine, BCAA = branched chain amino acids.

TABLE II

| | Muscle Amino Acid Concentrations (Mean ± SEM) (Expressed as mmol/l Intracellular Water) | | | | | | | | | |
|---|---|---|---|---|---|---|---|---|---|---|
| | Pre-operative | | | | | 24 Hours Post-Operative | | | | |
| Solution Infused | Total Nitrogen | GLN | Sum BCAA | Sum EAA*** | Sum NEAA | Total Nitrogen | GLN | Sum BCAA | Sum EAA | Sum NEAA |
| Saline | 69.8± 8.5 | 21.48± 3.21 | 0.437± 0.017 | 1.81± 0.23 | 40.92± 4.38 | 52.8± 9.4 | 15.86 ± 3.90* | 0.591 ± 0.0165 | 1.90± 0.32 | 31.50 ± 4.70** |
| Amino Acids (0.624 gm N/24 hr/kg) | 65.2± 10.3 | 18.69± 3.74 | 0.471± 0.074 | 2.24± 0.29 | 39.00± 6.10 | 62.5± 9.6 | 18.20 ± 3.75 | 0.795 ± 0.144 | 2.77± 0.36 | 36.70 ± 5.40 |
| Amino Acids + Glutamine (0.624 gm N/24 hr/kg) | 63.5± 7.0 | 19.85± 3.17 | 0.442± 0.022 | 1.99± 0.29 | 37.50± 3.82 | 68.3± 4.4 | 21.65 ± 2.08 | 0.773 ± 0.125* | 2.72± 0.22 | 39.74 ± 2.34 |

*p < 0.05, when compared to pre-operative value by paired t-test.
**p < 0.01, when compared to pre-operative value by paied t-test.
***EAA = essential amino acids; NEAA = non-essential amino acids.

TABLE III

| | Hindquarter Nitrogen Flux (Mean ± SEM; umol/min/kg) | | | | | |
|---|---|---|---|---|---|---|
| | 6-Hour Flux | | | 24-Hour Flux | | |
| Solution Infused | Total Amino Acid Nitrogen | GLN | BCAA | Total Amino Acid Nitrogen | GLN | BCAA |
| Saline | −19.05± | −2.69± | −1.41± | −3.50± | −1.71± | 0.49± |

TABLE III-continued

| Solution Infused | Hindquarter Nitrogen Flux (Mean ± SEM; umol/min/kg) 6-Hour Flux: Total Amino Acid Nitrogen | GLN | BCAA | 24-Hour Flux: Total Amino Acid Nitrogen | GLN | BCAA |
|---|---|---|---|---|---|---|
| Amino Acid (0.624 gm N/24 hr/kg) | 4.06* −7.70 ± 5.90 | 1.07 −1.93± 0.59 | 0.26** 1.62 ± 0.36 | 12.10 −8.42± 2.90 | 0.70 −1.24± 0.44 | 1.51 2.08± 1.53 |
| Amino Acids + Glutamine (0.624 gm N/24 hr/kg) | −6.52 ± 1.81 | −1.19± 0.46 | 0.28 ± 0.15 | −3.03± 3.75 | −0.16± 0.82 | 0.09± 0.22 |

*p < 0.05; saline different from all animals receiving 0.624 gm N/24 hr/kg.
**p < 0.01; saline < amino acids + glutamine < amino acids.
− = release
+ = uptake

TABLE IV

| Solution | Projected Nitrogen Intake (gm N/24 hr/kg) | N | Nitrogen Balance (Mean ± SEM) Nitrogen gm/24 hr/kg: Measured Intake | Excretion | Balance |
|---|---|---|---|---|---|
| Saline | 0 | 5 | 0 | 0.492 ± 0.022* | −0.492 ± 0.002** |
| Amino Acids*** | 0.312 | 2 | 0.304 ± 0.002 | 0.637 ± 0.056 | −0.332 ± 0.058 |
| Glutamine | 0.312 | 3 | 0.323 ± 0.003 | 0.709 ± 0.085 | −0.386 ± 0.086 |
| Amino Acids*** | 0.624 | 6 | 0.632 ± 0.001 | 0.694 ± 0.031 | −0.052 ± 0.031 |
| Amino Acids Plus**** | 0.624 | 6 | 0.635 ± 0.004 | 0.775 ± 0.019 | −0.140 ± 0.022 |

*p < 0.05; saline < 0.624 gm N/24 hr/kg amino acids < 0.624 amino acids + glutamine.
**p < 0.05; salne < 0.624 gm N/24 hr/kg amino acids + glutamine < 0.624 amino acids.
***FreAmine III
****One-half of nitrogen provided by FreAmine and one-half by glutamine.

EXAMPLE 5

Branched Chain Amino Acid Uptake and Muscle Free Amino Acid Concentrations Predict Postoperative muscle Nitrogen Balance To investigate the effectiveness of BCAA infusion to reduce skeletal muscle and whole body protein catabolism, amino acid formulas containing varying concentrations of BCAA were given perioperatively in this study to three groups of dogs undergoing a standard laparotomy and retroperitoneal dissection. A fourth group was given saline alone. Using hindquarter flux techniques, individual and total amino acid nitrogen exchange rates were measured and utilized in estimating skeletal muscle protein catabolism. Intracellular free amino acid concentrations were measured in percutaneous muscle biopsy samples. The work focuses on the effects of intravenous amino acid solutions containing varying concentrations of BCAA's on the regulation of skeletal muscle amino acid metabolism following a standardized surgical procedure in the dog. By measuring hindquarter amino acid flux and free amino acid concentrations in plasma and skeletal muscle during the first 24 hours following operation, it has been possible to evaluate the anticatabolic response to the infusion of BCAA's and other amino acids.

MATERIALS AND METHODS

Preparation of Animals and Sequence of Study

Twenty-seven male and non-pregnant female mongrel dogs were obtained from a farm where they had been conditioned and screened for parasites. The dogs weighed between 18 and 40 kilograms and were housed for at least one week prior to study in the Harvard Medical School animal car facility. All procedures were in accordance with the guidelines of the Committee on Animals at Harvard Medical School and the Committee on Car and Use of Laboratory Animals of the Institute for Laboratory Animal Resources, the National Research Council, supra. The animals were kept in individual kneels with 24-hour light exposure and were exercised each morning. Water was provided ad libitum and a single daily feeding of Pro-Pet Respond 2000 dry dog food (Syracuse, N.Y., at least 25% protein by weight) was provided between 1:00 and 3:00 p.m. The animals were trained to rest quietly in a Pavlov sling prior to study.

All food was removed from the kennels at 5:00 p.m. the night before basal studies or operation. Basal studies were performed at 8:00 a.m. after the animal was exercised and placed in the sling. These studies consisted of the collection of a blood sample from a cannulated foreleg vein for plasma amino acid determination and a percutaneous needle biopsy of the vastus lateralis muscle performed under sodium thiopental anesthesia (Abbott, North Chicago, Ill., 5 mg/kg body weight, IV) to quantitate intracellular free amino acids. After the biopsy, with the dog still anesthetized, a 5 ml sample of arterial blood was obtained by percutaneous puncture of the femoral artery to analysis of whole blood amino acids.

The animal was allowed to recover for three days before further studies were performed. At 7:00 a.m. on the day of operation, again after an overnight fast, the animal was exercised and taken to the operating room where it was anesthetized with sodium pentobarbital (Abbott, North Chicago, Ill., 30 mg/kg body weight, IV) via a foreleg cannula. An endotracheal tube was placed and the animal was allowed to breathe spontaneously a mixture of room air and oxygen provided at 5 L/minute. The dog was placed on an operating table in the supine position and a 16-Fr. catheter was placed percutaneously into the superior vena cava via the external jugular vein. After noting the starting time, an infusion of either saline or the appropriate test amino acid solution was begun via this central catheter with an IMED pump (San Diego, Calif.). Caphalothin (Lilly, Indianapolis, Ind. 1 gram, IV) was given immediately before and upon completion of the operation. The urinary bladder was catheterized and, after discarding residual urine, a closed drainage collection was begin at the start of the infusion and carried on for 24 hours. Urine was also collected for a second 24-hour period, with the animal in a metabolic cage after termination of the IV infusion.

The abdomen and flanks of the dog were shaved, washed with soap and water, and prepped with a povidone iodine solution. The animal was sterilely draped, and the abdomen was entered via an infra-umbilical midline incision in females and a right paramedian incision in males. The bowel was retracted aside, and the retroperitoneum exposed for complete dissection around the distal aorta and inferior vena cava. The right deep circumflex iliac artery and vein as well as the right internal iliac artery were isolated. The two arteries were cannulated with specially prepared catheters consisting of a 6-cm segment of polyethylene tubing (2.08 mm O.D.) linked to 2.8 mm O.D. polyethylene tubing. One arterial catheter was positioned 6 cm proximally into the aorta via the circumflex iliac artery and the other catheter positioned one cm proximal to the aortic bifurcation, but distal to the caudal mesenteric artery, via the internal iliac artery. A third catheter was inserted into the inferior vena cava via the deep circumflex iliac vein and positioned distal to the renal vein. All catheters were secured and exteriorized through stab would in the right flank. The abdomen was closed in layers and the animal turned on its left side. The exteriorized catheters were cut to appropriate lengths, plugged with blunt needles, capped with intermittent injection ports (Jelco, Critikon, Tampa, Fla.), flushed with saline, filled with heparin (100 uU/ml), and buried subcutaneously. The injection ports were positioned high in the flanks allowing easy access to arterial (aortic) and venous (vena caval) blood by percutaneous puncture.

Following these procedures, which generally took two hours, the animal was placed on its side and body temperature was maintained with blankets during recovery from anesthesia. Five hours after the start of the infusion and operation, the animal was placed in the Pavlov sling and a solution of 0.5% para-aminohippurate (PAH) was infused at a rate of 0.7 ml/minute with a Harvard pump into the distal aortic catheter. After 40 minutes of dye infusion, three sets of simultaneous arterial and venous samples were obtained at 10-minute intervals for measurement of amino acid and PAH concentrations. The catheters were then flushed and filled with heparin. The animal was kept in the sling under constant surveillance until the hindquarter flux studies were repeated 24 hours after the start of the infusion. At this point, the first 24-hour urine collection was terminated, and a repeat percutaneous hind limb biopsy was performed on the leg not previously biopsied, again under brief general anesthesia. The infusion was then terminated and the animal placed in a metabolic cage for the second 24-hour period.

Infusion Solutions

All solutions were infused at the rate of 4 ml/minute/kg. five control animals received 0.9% saline. Amino acid solutions (Table V) containing BCCA's at three different concentrations (11%, 22%, or 44% of total amino acids) were prepared by adding amino acids to an 8.5% standard amino acid formula, FreAmine III (American McGaw, Irvine, Calif.). The total BCAA infusion rates were 0.46, 0.92, and 1.84 grams/24 hours/kg, respectively. All three amino acid solutions were isonitrogenous, providing approximately 0.624 grams of nitrogen/24 hours/kg, with a constant ratio of valine to leucine to isoleucine (1:1.38:1.05). Nine animals received al 11% BCAA solution which was made by dissolving a mixture of non-essential amino acids (NEAA) in 2.13% FreAmine III to make a solution that provided 0.624 grams of nitrogen/24 hours/kg. In 6 animals, NEAA consisted of L-glutamine alone and in three, NEAA consisted of a mixture of all of the NEAA found in FreAmine III (alanine, glycine, arginine, histidine, serine, and proline) in the same ratios as in FreAmine III. Six animals received 4.25% FreAmine III alone (22% BCAA). The final 7 animals received 2.13% FreAmine III supplemented with enough BCAA's to make a 44% solution. This final formula was made isonitrogenous by adding NEAA as L-glutamine alone (n=4) or a mixture of the NEAA found in FreAmine III (n=3). All solutions were sterilized by passage through a 0.22 uM filter (Millipore, Millis, Mass.) and stored overnight at 4° C. prior to administration A 10-ml sample of each solution was taken at the end of the infusion period and stored at −20° C. for analysis of nitrogen by the macro-Kjeldahl method.

Preparation and Analysis of Blood, Tissue, and Urine Samples

Whole blood and plasma samples were deproteinized by adding an equal volume of ice-cold 10% perchloric acid (PCA) and then centrifuging at 7000 rpm at 4° C. for 20 minutes. A 2-ml aliquot of the supernatant was buffered with 0.3 ml of 0.2 M sodium acetate buffer (pH=4.90), adjusted to pH 4.75–4.90 with 5N potassium hydroxide, brought to a final volume of 4 ml with distilled water, and centrifuged again. The resulting supernatant was stored at −20° C. for later batch analysis.

During the muscle biopsy procedure, a stopwatch was started at the time of tissue removal. The muscle was dissected free of fat and connective tissue and divided into two unequal portions. Multiple weights on each sample were recorded at 15-second intervals for one minute, and the initial muscle wet weight at time=0 was calculated from the best fit linear regression of weight plotted against time. The smaller sample (approximately 15–20 mg) was dried to a constant weight in an oven at 90° C., and the weight of dried fat-free solids was obtained after extraction in petroleum ether. The sample was then soaked in 250 ml of 1 n nitric acid, and the chloride content was measured by titration with silver nitrate using a semi-automated titrator (Radiometer, Copenhagen). Plasma chloride was also determined by a similar method. Intracellular and extracellular water were then calculated using the chloride technique, as previously described. The second muscle sample (approximately 80–100 mg) was weighed and homogenized in 0.5 ml of ice-cold PCA using a Polytron homogenizer (Brinkmann, Westbury, N.Y.). The homogenate was centrifuged, and the supernatant was prepared for analysis by addition of buffer and by pH adjustment to pH 4.75–4.90 as described for blood and plasma samples.

Whole blood, plasma, and muscle intracellular glutamine and glutamate concentrations were determined by an enzymatic microfluorometric method modified from the method of Lund, P., "L-glutamine determination with glutaminase and glutamate dehydrogenase," In: Methods of Enzymatic Analysis, Bergmeyer HU, ed., Vol. 4, New York: Academic Press 1719–1722 (1974), or by automated high performance liquid chromatography (HPLC) after pre-column derivation with o-phthaladehyde, Smith, R. J., et al., "Automated analysis o-phthalaldehyde derivatives of amino acids in physiological fluids by reverse phase high performance liquid chromatography," J. Liq. Chromatog. 8:1783–1795 (1985). The two techniques yielded comparable results. Other amino acids except proline, cystine, and lysine were determined with a similar HPLC method. The concentration of PAH in the arterial and venous blood was determined spectrophotometrically following deproteinization with 5% trichloroacetic acid, Muhlbacher F., et al., "Effects of glucocorticoids on glutamine metabolism in skeletal muscle," Am. J. Physiol. 247:E75-E83 (1984).

Urine excreted during the 24 hours of infusion was collected in a closed urinary drainage system and stored in acidified, refrigerated containers. Aliquots were stored frozen at −20° C. for later batch analysis of nitrogen by the macro-Kjeldahl method, Peters J. P., et al., "Total and non-protein nitrogen," In: Quantitative Clinical Chemistry, Vol. II, 516–538, Baltimore: Williams & Williams, (1932). Another portion was centrifuged for 10 minutes at 2000 rpm and frozen for later analysis of urea and creatinine on the Technicon Auto-analyzer (Tarrytown, N.Y.).

Calculations and Statistical Analysis

Hindquarter bloodflow was calculated as previously described (Muhlbacher, F. et al., supra). Flux rates for the individual amino acids were calculated as the product of bloodflow and arteriovenous concentration difference. Three sets of samples were drawn at each time point, the flux was calculated for each set, and the mean of the three values was determined. Total amino acid nitrogen flux as well as plasma, whole blood, and intracellular nitrogen concentrations were calculated as the millimolar sum of the nitrogen groups of all amino acids measured. Skeletal muscle free intracellular amino acid concentrations were expressed per liter of intracellular water.

Statistical calculations were performed using a standard statistical package (Minitab, The Pennsylvania State University, State College, Pa., 1983). The results are expressed as mean ± SEM. Paired and unpaired Student's t-tests were used as appropriate. Analysis of variance was used for multiple group comparisons. Regression analysis was performed using the method of least squares.

Results

All animals survived the operative procedure except for one dog that died shortly after administration of sodium pentobarbital, before the start of the intravenous infusion. This animal was not included in the study. Blood loss during the procedure was uniformly minimal. All sample catheters were patent at the 6- and 24-hour time points, with the exception of one venous catheter at the 24-hour time point in an animal in the 22% BCAA group.

Hindquarter bloodflow at 6 hours was 36.1±6.8 ml/minute/kg in the saline control group and was not by treatment (11% BCAA, 33.3±4.9; 22% BCAA, 42.4±8.8; 44% BCAA, 28.7±3.5; differences not significant). Flow at 24 hours was unchanged (57.9±10.2, 38.6±8.2, 54.9±6.5, 49.7±13.2, respectively). The tendency toward higher flow rates and increased variability at 24 hours may be attributable to greater motor activity of the animals following from anesthesia recovery.

Urinary Nitrogen Excretion and Nitrogen Balance

Following operation, the volume of urine excreted was comparable in the four treatment groups, although the dogs receiving saline alone tended to excrete less urine volume (Table VI). Urinary nitrogen excretion averaged 0.492±0.20 grams/24 hours kg in the saline group. The amino acid treated animals excreted 35–65% more nitrogen than the saline group, primarily in the form of urea, the dogs infused with the 22% BCAA solution excreted significantly less urea nitrogen and less total nitrogen than the 11% or 44% BCAA groups. Excretion of creatinine and ammonia was comparable in all groups.

Blood urea nitrogen and plasma creatinine were measured before and 24 hours following operation in selected animals from all groups. These concentrations were normal in all animals before operation and fell slightly or did not change postoperatively. Thus, the rate of urinary excretion of urea was similar to the rate of urea production; the higher urea production observed in the animals receiving the 11% and 44% BCAA solutions was significantly related ($p<0.05$) to the extra nitrogen provided by addition of BCAA or NEAA to the balanced amino acid mixture.

Nitrogen balance was less negative with amino acid administration; approximately 50% of the infused amino acid nitrogen was retained. Because nitrogen intake was the same in all animals receiving amino acids, the alterations in nitrogen excretion already discussed were reflected in nitrogen balance (Table VI). Thus, the animals receiving the 22% balanced amino acid solution achieved significantly greater nitrogen retention than the dogs receiving solutions containing 11% or 44% BCAA.

Whole Blood Amino Acid Concentrations

In the saline-treated animals, whole blood amino acid nitrogen fell at 6 hours postoperation, but returned to normal preoperative levels by 24 hours (Table VII). This transient hypoaminoacidemia was accounted for in large part by a decrease in the concentration of the non-essential amino acids (glutamine, alanine, arginine, serine, and asparagine), although significant decreases in some essential amino acids also occurred (threonine and tyrosine). In contrast, the animals receiving amino acid infusions maintained whole blood amino acid nitrogen concentrations at 6 hours postoperation. These levels increased above preoperative control levels by 24 hours ($p<0.05$).

Figure 2:
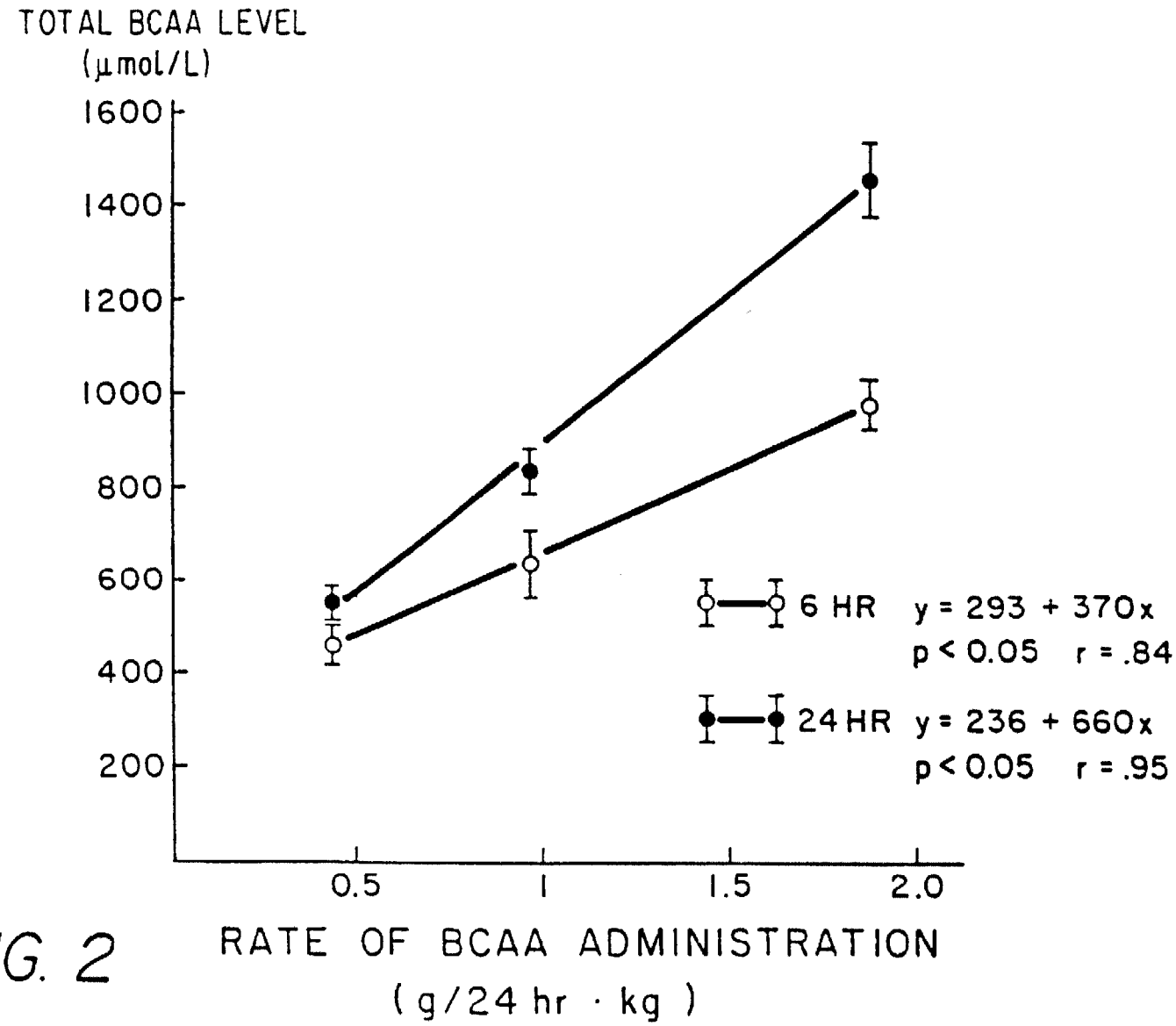
FIG. 2 is a graphic presentation of data generated in Example 5 comparing total branch chain amino acid (BCAA) level in arterial blood with the rate of administration of BCAA. Data represents mean ± SEM. Data from animals receiving saline is not included.

Concentrations of specific amino acids in the blood of the animals receiving amino acid infusions reflected the composition of the solutions infused. For example, BCAA concentrations were related to the rate of BCAA administration at both 6 and 24 hours (FIG. 2). In general, whole blood glutamine concentrations at 6 hours were lower than preoperative levels (Table VII). The exception was the group receiving glutamine enriched 11% BCAA solution, in which the blood glutamine concentration was maintained. In these animals, glutamine comprised more than one-half of the non-essential nitrogen and accounted for more than 40% of the total amino acids delivered. By 24 hours the animals receiving glutamine-containing infusions tended to have higher than normal whole blood glutamine concentrations.

Skeletal Muscle Intracellular Free Amino Acids

In the saline-treated animals, intracellular free amino acid nitrogen fell significantly by 24 hours postoperation when compared to preoperative levels (Table VIII). This change was accounted for in large part (65%) by the marked fall in intracellular glutamine, which comprised a major portion of the total intracellular free amino acid pool. In the animals receiving amino acid infusions, intracellular nitrogen was maintained, although intracellular glutamine fell in the animals that received the glutamine-free 11% BCAA solution. Intracellular glutamine tended to increase in the animals receiving glutamine-enriched solutions and BCAA concentrations increased in proportion to the rate of BCAA infusion.

Hindquarter Amino Acid Flux

In the saline-treated animals there was net release of amino acid nitrogen from the hindquarter at 6 hours postoperation (Table IX). This increased amino acid efflux reflected accelerated release of almost all amino acids measured, including the BCAA. At this time period, glutamate and aspartate were the only amino acids that maintained balance across the hindquarter. At 24 hours postoperation, the rate of hindquarter amino acid nitrogen release had diminished and, although highly variable, the arteriovenous differences for almost all amino acids could not be distinguished from zero. Glutamine efflux persisted at this time point.

Figure 3:
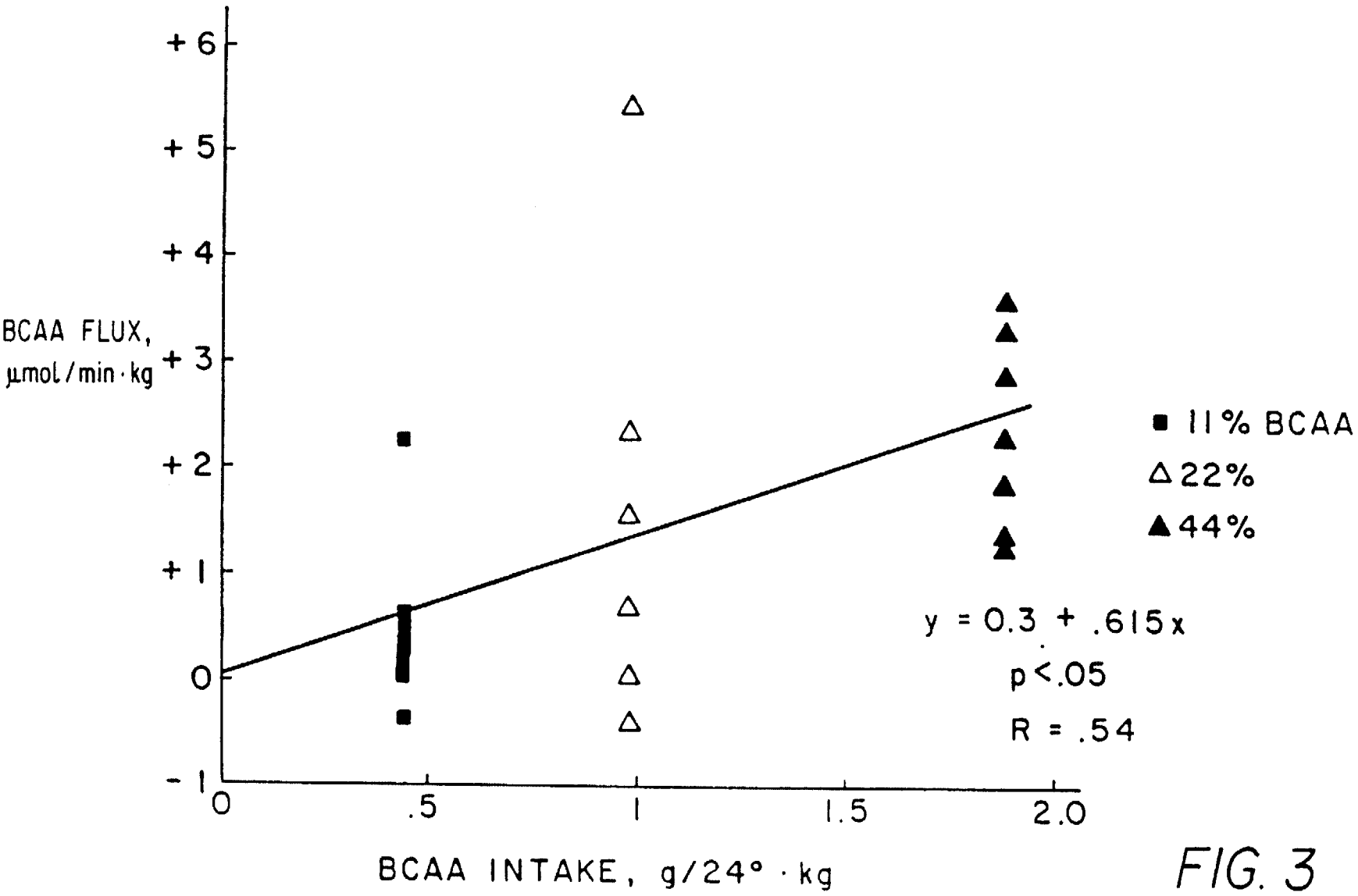
FIG. 3 is a graphic presentation of data generated in Example 5 comparing the relationship between BCAA flux (hindquarter) and BCAA infusion.
Figure 4:
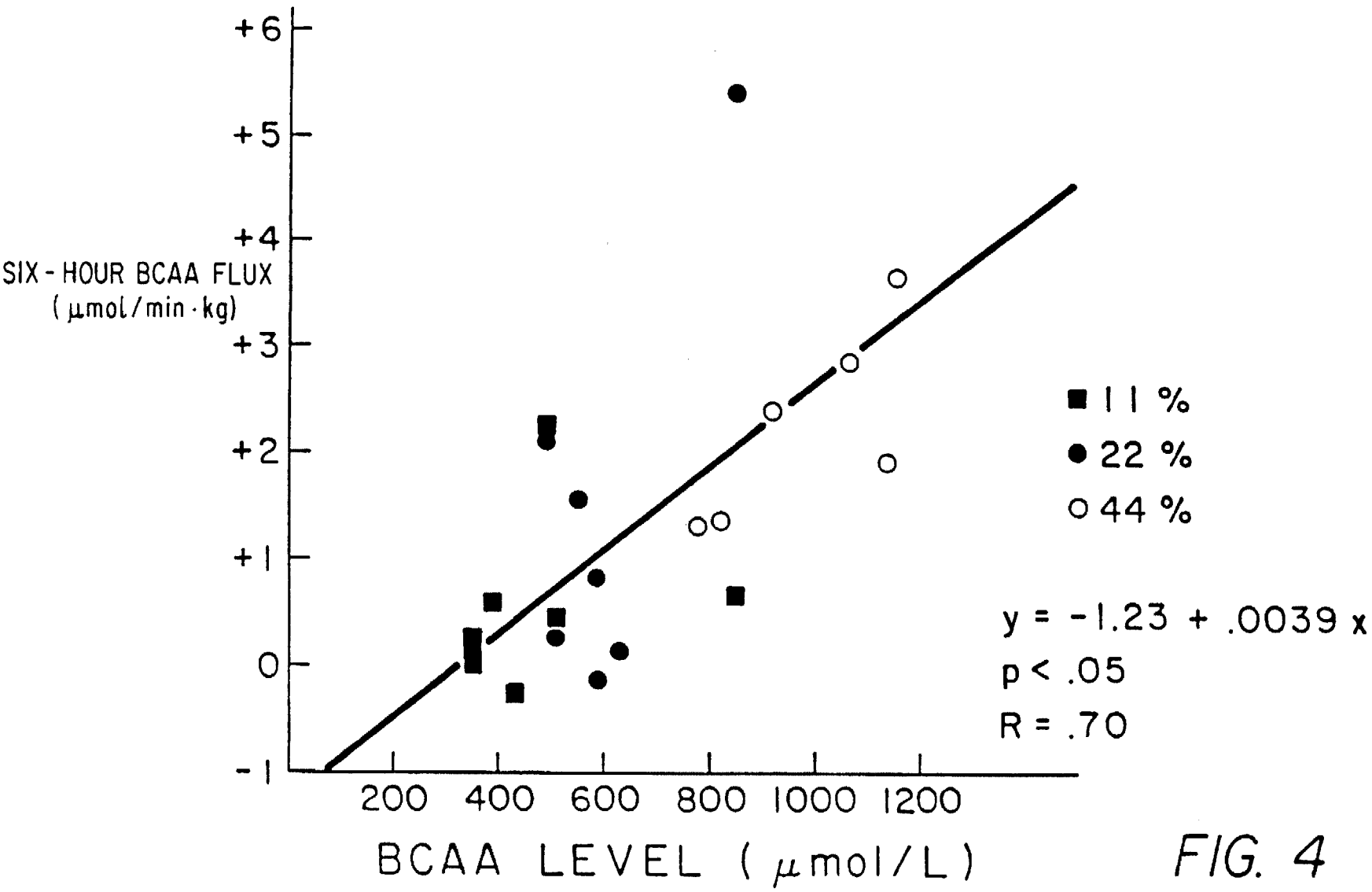
FIG. 4 is a graphic presentation of data generated in Example 5 comparing BCAA flux (hindquarters) six hours postoperative and the increase in concentration of BCAA arterial blood level.

In all groups of animals receiving amino acid infusions, hindquarter amino acid nitrogen efflux at 6 hours was similar and was significantly less than in the saline-treated animals ($p<0.05$). Both glutamine and alanine efflux at 6 hours tended to be less in the animals receiving amino acids than in the saline controls. While BCAA's were released at 6 hours in the saline-infused animals, these amino acids were taken up in the dogs receiving amino acid infusions. BCAA hindquarter uptake was related to the rate of BCAA administration (FIG. 3) and whole BCAA concentrations (FIG. 4).

At 24 hours, hindquarter amino acid nitrogen efflux was similar in all the amino acid infusion groups and unchanged compared to 6 hours. At 24 hours, BCAA hindquarter exchange was slightly positive, tending to be greater in the 22% and 44% BCAA groups. At this time, BCAA update was unrelated to blood concentrations and rate of BCAA administration.

Figure 5:
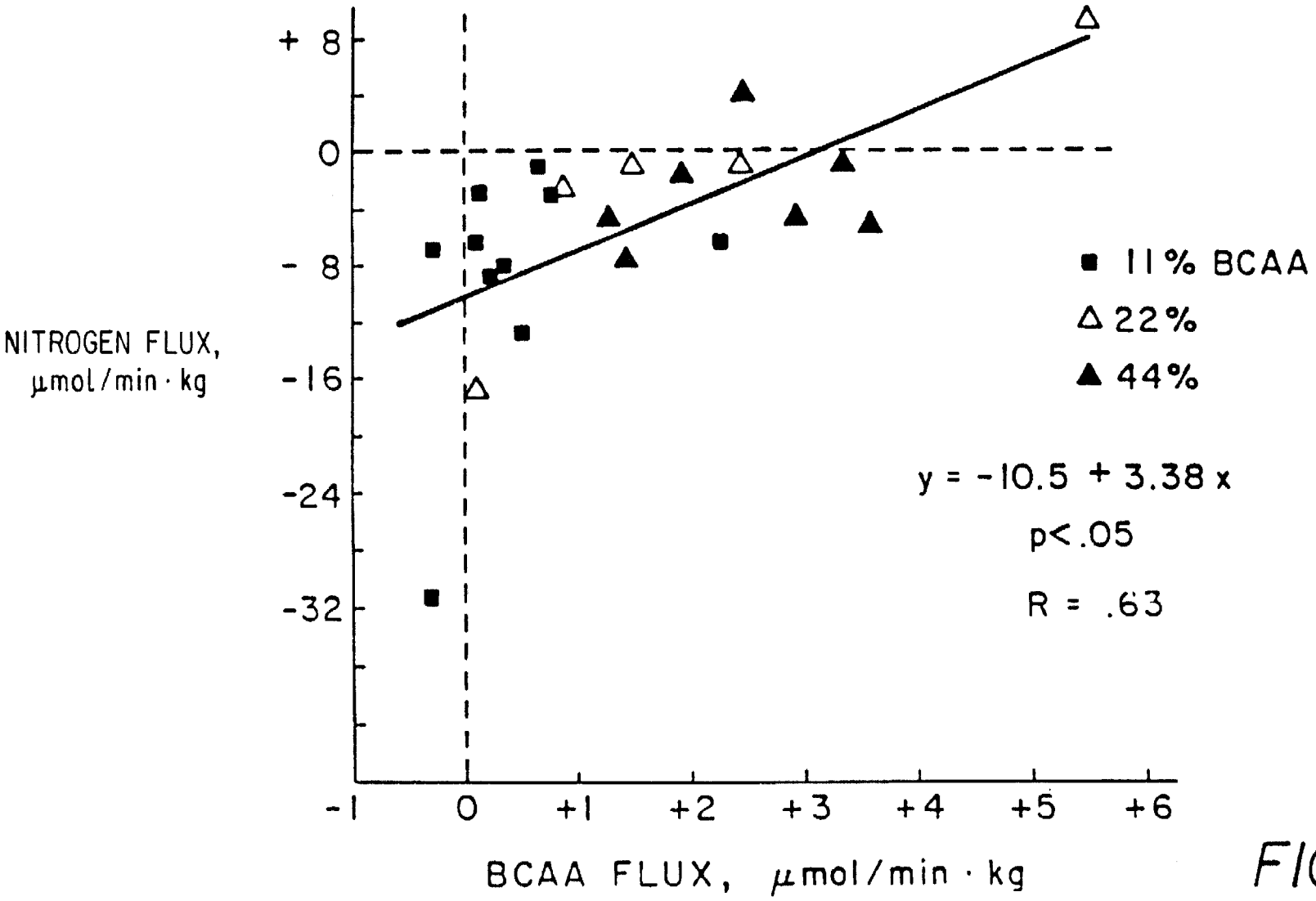
FIG. 5 is a graphic presentation of data generated by Example 5 comparing nitrogen flux (hindquarter) and BCAA flux (hindquarter) six (6) hours post-operation.

Relationship Between BCAA Infusion, BCAA Hindquarter Uptake, and Hindquarter Amino Acid Nitrogen Release In the saline-infused dogs at 6 hours, hindquarter BCAA release was associated with accelerated amino acid efflux. In the animals receiving amino acid infusions, the hindquarter nitrogen balance correlated with BCAA uptake (FIG. 5). Saline controls were not included in this analysis since they were not receiving nitrogen; inclusion of control animals would have resulted in a regression line with a more positive slope. The correlation was maintained even if BCAA flux was not included in the summation of hindquarter amino acid nitrogen flux ($p<0.02$, $r=0.49$). Thus, nitrogen flux exclusive of BCAA flux was also related to BCAA uptake. Nitrogen flux did not correlate with total BCAA concentration in the blood or the rate of BCAA administration. None of these relationships existed at the 24-hour time point.

Figure 6:
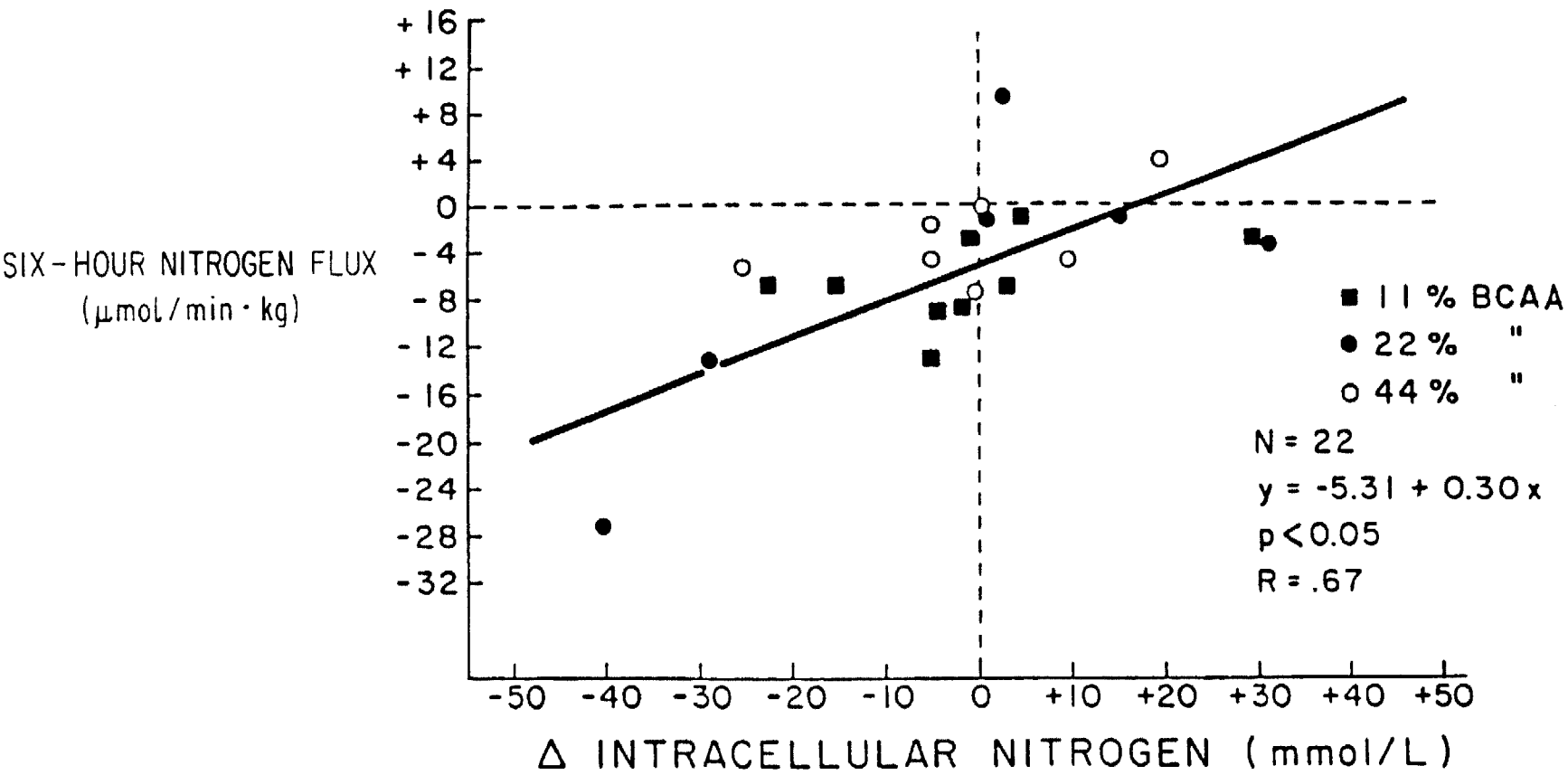
FIG. 6 is a graphic presentation of data generated in Example 5 comparing nitrogen flux (hindquarter) six (6) hours post-operation and the change in muscle intracellular amino acid nitrogen measured 24 hours post-operation.

Hindquarter amino acid nitrogen release at 6 hours also correlated with changes in the intracellular free amino acid nitrogen pool (FIG. 6). Alterations in intracellular glutamine were closely related to changes in the total free amino acid nitrogen pool ($p<0.001$, $r=.90$) and, thus, changes in the glutamine pool were also significantly related to hindquarter nitrogen efflux ($p<0.05$; $r=0.66$). These mathematical relationships were maintained when hindquarter amino acid nitrogen efflux was corrected for changes in the intracellular nitrogen pool. Since the flux and pool measurements were made at different points in time, we made this correction by assuming two different rates of change in the intracellular amino acid pool. First, it was assumed that the change in the intracellular pool occurred in the first 6 hours postoperatively. Alternatively, it was assumed that the change occurred at a constant rate over 24 hours. Neither correction altered the relationship between the change in the intracellular nitrogen pool and amino acid nitrogen efflux.

BCAA uptake was not related to increased glutamine release from the hindquarter at 6 or 24 hours. BCAA uptake was also unrelated to the changes that occurred in the skeletal muscle intracellular free amino acid pool ($r=0.11$, not significant). Hindquarter nitrogen flux could be predicted and most of the variability in the data could be accounted for when both BCAA 6-hour flux and the change in the free amino acid nitrogen pool were utilized. The relationship was:

$$= -9.58 + 0.27\ x_1 + 3.02\ x_2$$

where, $y$ = amino acid nitrogen flux at 6 hours, umol/min/kg $x_1$ = BCAA flux at 6 hours (umol/min/kg $x_2$ = change in skeletal muscle intracellular free amino acid nitrogen (postop — preop, mmol/L24 hours)

$n = 22$, $p < .05$, $r = 0.86$

DISCUSSION

A standardized laparotomy in anesthetized dogs has been shown to initiate many of the catabolic responses observed in critically ill humans. Total body protein catabolism, as measured by urinary nitrogen excretion, is increased. The control animals receiving saline excreted approximately 12–15 grams of nitrogen in the first 24 hours following operation. Prior studies in this model have demonstrated that nitrogen balance remains negative for three days following the operative procedure in spite of food intake. Kapadia, C. R., et al., "Alterations in glutamine metabolism in response to operative stress and food deprivation," Surg. Forum 33:19–21 (1982). In contrast, pair-fed sham-operated animals achieved nitrogen equilibrum in the first postoperative day. Consistent with and contributing to the increased urinary nitrogen loss, hindquarter release of total amino acid nitrogen at 6 hours following operation was 6 to 8 times that observed in control animals after an over-night fast (Muhlbacker, F., et al., supra). Other changes in the saline-treated dogs, such as a decrease in blood and skeletal muscle amino acid concentrations are similar to alterations reported during catabolic states in humans, Askanazi J., et al., "Muscle and plasma amino acids following injury: influence of intercurrent infection," Ann. Surg. 192:78–85 (1980). Thus, the canine model exhibits postoperative responses that are similar to alterations in critically ill humans and, therefore, is suitable for examining the effects of exogenous amino acids on nitrogen metabolism and skeletal muscle amino acid exchange.

In the saline-treated animals, hindquarter release of amino acid nitrogen was markedly increased 6 hours postoperatively. This was associated with a net skeletal muscle release of all the BCAA's. At the same time, whole blood BCAA concentrations were un changed, indicating that consumption of BCAA in visceral organs was roughly equivalent to the accelerated rate of skeletal muscle release. In the animals receiving amino acids, hindquarter total amino acid release was attenuated, whole blood and skeletal muscle nitrogen pools were maintained, the hindquarter was converted from an organ of BCAA release to one of uptake. BCAA, and more specifically, leucine uptake was not associated with increased skeletal muscle release of glutamine.

This study demonstrates that skeletal muscle amino acid release and, hence, the net turnover of muscle protein, can be predicted from two independent measurements. These are the rate of BCAA flux across the skeletal muscle vascular bed and the concentration of nitrogen in the skeletal muscle free amino acid pool. Since glutamine is the most abundant amino acid in the free pool, changes in its concentration largely determine changes in the total pool. In fact, changes in the free glutamine predict muscle nitrogen balance as well as changes in total free amino acids.

TABLE V

COMPOSITION OF INFUSED SOLUTIONS (EXPRESSED AS GRAMS INFUSED/24 HOURS/KG)

| | | ESSENTIAL AMINO ACIDS | | NON-ESSENTIAL AMINO ACIDS | | |
|---|---|---|---|---|---|---|
| SOLUTION | | BCAA* | OTHER | GLUTAMINE | OTHER | TOTAL NITROGEN |
| SALINE | 5 | 0 | 0 | 0 | 0 | 0 |
| 11% BCAA* + GLUTAMINE | 6 | 0.46 | 0.54 | 1.64 | 1.04 | 0.62 |
| 11% BCAA* + NEAA** | 3 | 0.46 | 0.54 | 0 | 2.77 | 0.62 |
| 22% BCAA* = SAA*** | 6 | 0.92 | 1.09 | 0 | 2.07 | 0.62 |
| 44% BCAA* + GLUTAMINE | 4 | 1.84 | 0.54 | 0.82 | 1.04 | 0.62 |
| 44% BCAA* + NF-AA-1 | 3 | 1.84 | 0.54 | 0 | 1.90 | 0.62 |

*BCAA = Branched chain amino acids (valine, leucine, isoleucine)
**NEAA = Non-essential amino acids found in FreAmine III ® (American McGaw) (alanine, arginine, glycine, histidine, proline, serine)
***SAA = Standard amino acids supplied as FreAmine III ®

TABLE VI

VOLUME AND COMPOSITION OF 24-HOUR URINARY EXCRETION

| INFUSION | N | VOLUME (ml/kg) | NITROGEN INTAKE (g/kg) | TOTAL NITROGEN EXCRETION (g/kg) | NITROGEN BALANCE (g/kg) | UREA N EXCRETION (g/kg) | CREATININE EXCRETION (g/kg) | AMMONIUM EXCRETION (g/kg) |
|---|---|---|---|---|---|---|---|---|
| SALINE | 5 | 43.3 ± 10.2 | 0* | 0.492 ± .02* | −0.492 ± .02* | 0.409 ± .03* | 0.039 ± .002 | 0.037 ± .005 |
| 11% BCAA | 9 | 57.5 ± 6.9 | 0.627 ± .005 | 0.786 ± .02 | −0.160 ± .02 | 0.697 ± .01 | 0.033 ± .001 | 0.049 ± .004 |
| 22% BCAA | 6 | 64.2 ± 5.1 | 0.632 ± .001 | 0.685 ± .03** | −0.053 ± .03** | 0.603 ± .03** | 0.034 ± .002 | 0.045 ± .005 |
| 44% SCAA | 7 | 74.0 ± 8.2 | 0.627 ± .003 | 0.825 ± .05 | −0.200 ± .05 | 0.701 ± .04 | 0.037 ± .002 | 0.041 ± .003 |

*Saline diff. from treatment groups, $p < 0.05$.
**Diff. from other 2 treatment groups, $p < 0.05$.

TABLE VII

WHOLE BLOOD AMINO ACID PROFILE (μMOL/L, MEAN ± SEM)

| | | | | 11% BCAA | | | | | |
|---|---|---|---|---|---|---|---|---|---|
| | SALINE | | | GLN | | | NEAA | | |
| | PRE | 6° | 24° | PRE | 6° | 24° | PRE | 6° | 24° |
| GLN | 724.0± 55 | 565.0± 53 | 764.0± 64 | 764.0± 63 | 754 ± 57 | 1108 ± 110 | 808 ± 111 | 626.0± 20.6 | 679.9± 55.2 |
| ALA | 431.9± 42.6 | 257.9± 13.4 | 325.0± 56 | 429.0± 38.8 | 270.7± 35.1 | 290.9± 14.8 | 344.1± 81 | 364.0± 101 | 481.0± 152 |
| GLY | 414.0± 90 | 212.0± 14.5 | 239.9± 16.1 | 439.0± 57 | 419.0± 63 | 469.0± 60 | 194.3± 38.7 | 509.5± 34.4 | 595.0± 89 |
| ARG | 241.2± 27 | 152.5± 7.9 | 175.0± 9.1 | 262.1± 39.3 | 221.5± 18.2 | 265.9± 23.1 | 177.1± 29.6 | 229.8± 33.1 | 296.2± 41.2 |
| SER | 131.4± 9.3 | 96.8± 8.1 | 140.4± 8.4 | 166.7± 22. | 142.3± 5.7 | 179.3± 11.7 | 118.0± 24.8 | 221.5± 22.2 | 293.6± 36.9 |
| ASP | 29.8± 5.4 | 27.6± 4.6 | 29.3± 4.2 | 30.3± 3.7 | 25.9± 2.8 | 30.6± 3.4 | 27.1± 2.8 | 23.4± 4.1 | 22.3± 3.9 |
| ASN | 39.7± 4.9 | 26.7± 2.1 | 54.7± 2.6 | 48.0± 3.8 | 31.6± 1.1 | 50.4± 3.9 | 54.1± 8.7 | 33.1± 4.6 | 47.6± 8.0 |

TABLE VII-continued

| WHOLE BLOOD AMINO ACID PROFILE (μMOL/L, MEAN ± SEM) | | | | | | | | | |
|---|---|---|---|---|---|---|---|---|---|
| GLU | 65.8 ± 4.7 | 68.0 ± 4.1 | 72.3 ± 3.9 | 66.1 ± 4.3 | 67.1 ± 5.0 | 66.9 ± 2.6 | 66.0 ± 10.7 | 75.8 ± 11.4 | 63.6 ± 4.9 |
| MIS | 109.8 ± 8.3 | 108.0 ± 11.9 | 122.0 ± 10.1 | 105.1 ± 14.3 | 115.9 ± 10.0 | 133.9 ± 10.0 | 88.2 ± 6.0 | 116.8 ± 6.6 | 133.1 ± 11.9 |
| TYR | 72.8 ± 7.3 | 54.9 ± 1.2 | 66.2 ± 4.8 | 91.3 ± 24.6 | 53.3 ± 5.0 | 63.9 ± 4.9 | 52.1 ± 5.7 | 45.1 ± 0.1 | 54.3 ± 3.9 |
| TAU | 264.3 ± 39.3 | 411.0 ± 46 | 441.3 ± 29.5 | 346.0 ± 73 | 467.0 ± 58 | 474 ± 62 | 317.5 ± 45.1 | 401.3 ± 45.9 | 459 ± 65 |
| MET | 12.3 ± 0.9 | 16.6 ± 1.9 | 40.8 ± 2.6 | 42.2 ± 10.2 | 33.9 ± 6.2 | 54.3 ± 9.5 | 25.7 ± 3.0 | 20.7 ± 8.4 | 33.1 ± 6.8 |
| THR | 239.0 ± 29 | 160.5 ± 28.4 | 281.7 ± 28.7 | 264.0 ± 66 | 204.6 ± 30.5 | 306.3 ± 35.9 | 241.9 ± 24.5 | 245.2 ± 15.9 | 277.0 ± 67 |
| PHE | 44.7 ± 4.1 | 52.9 ± 4.6 | 69.3 ± 4.7 | 45.9 ± 5.4 | 74.2 ± 5.8 | 89.7 ± 5.7 | 41.9 ± 3.1 | 66.3 ± 2.0 | 82.5 ± 4.4 |
| VAL | 149.5 ± 11.3 | 143.4 ± 8.4 | 210.3 ± 13.9 | 165.9 ± 24.5 | 225.1 ± 32.0 | 250.5 ± 22.9 | 135.2 ± 16.8 | 203.9 ± 18.0 | 271.0 ± 10.2 |
| ILE | 53.1 ± 5.0 | 54.4 ± 3.8 | 85.7 ± 4.2 | 55.9 ± 5.8 | 97.3 ± 14.1 | 112.6 ± 9.5 | 45.4 ± 7.1 | 90.0 ± 9.5 | 121.6 ± 4.4 |
| LEU | 102.7 ± 7.4 | 96.2 ± 7.1 | 153.2 ± 7.3 | 105.2 ± 5.6 | 153.2 ± 29.7 | 166.6 ± 15.8 | 99.0 ± 19.0 | 140.7 ± 16.3 | 179.6 ± 5.8 |
| TOTAL BCAA | 305.3 ± 23 | 294.0 ± 17.6 | 449.3 ± 24.8 | 322.31± 30.9 | 475.6 ± 68.1 | 534.7 ± 51.9 | 279.6 ± 35.0 | 434.6 ± 35.7 | 562.1 ± 9.2 |
| TOTAL NITROGEN | 4.72± .36 | 3.82± .08 | 4.87± .20 | 5.27± .38 | 5.06± .20 | 6.69± .44 | 4.40± .50 | 5.00± .31 | 5.96± .64 |

| | 22% BCAA | | | 44% BCAA | | | | | |
|---|---|---|---|---|---|---|---|---|---|
| | | | | GLN | | | NEAA | | |
| | PRE | 6° | 24° | PRE | 6° | 24° | PRE | 6° | 24° |
| GLN | 693.0 ± 77 | 493.6 ± 29.7 | 648.7 ± 38.3 | 961.0 ± 130 | 723.6 ± 44.2 | 1040 ± 66 | 861.5 ± 40.5 | 607.0 ± 23.4 | 558.0 ± 33.5 |
| ALA | 379.0 ± 62 | 327.7 ± 38.0 | 366.0 ± 43 | 407.0 ± 55 | 242.2 ± 29.6 | 240.3 ± 9.7 | 372.0 ± 103 | 362.6 ± 49.1 | 359.1 ± 34.9 |
| GLY | 381.0 ± 67 | 521.9 ± 33.3 | 559 ± 51 | 247.0 ± 32.9 | 330.1 ± 88 | 255.4 ± 18.2 | 243.3 ± 51.4 | 376.7 ± 28.2 | 420.7 ± 16 |
| ARG | 208.9 ± 19.7 | 254.8 ± 8.3 | 323.8 ± 19.3 | 185.2 ± 17.4 | 184.9 ± 8.8 | 181.5 ± 5.6 | 191.2 ± 1.8 | 229.2 ± 15.0 | 261.9 ± 9.3 |
| SER | 126.2 ± 7.9 | 162.4 ± 11.0 | 223.9 ± 12.1 | 130.6 ± 6.3 | 135.5 ± 7.9 | 143.2 ± 11.9 | 153.6 ± 14.1 | 188.2 ± 8.9 | 226.6 ± 18 |
| ASP | 21.6 ± 1.9 | 19.9 ± 1.8 | 24.6 ± 1.3 | 39.1 ± 12.2 | 27.6 ± 2.1 | 21.7 ± 1.0 | 27.4 ± 4.1 | 24.6 ± 2.8 | 21.7 ± 1.7 |
| ASN | 37.9 ± 6.8 | 22.9 ± 2.1 | 37.1 ± 4.1 | 56.1 ± 4.7 | 32.0 ± 1.9 | 47.6 ± 3.3 | 55.6 ± 2.8 | 26.3 ± 1.0 | 38.4 ± 4.6 |
| GLU | 51.2 ± 4.3 | 51.74± 3.2 | 55.7 ± 2.5 | 62.0 ± 2.8 | 68.3 ± 3.9 | 59.5 ± 4.0 | 72.6 ± 9.6 | 66.4 ± 9.8 | 50.9 ± 7.4 |
| MIS | 100.3 ± 7.1 | 121.2 ± 15.6 | 136.7 ± 11.7 | 104.2 ± 5.8 | 119.9 ± 11.2 | 103.1 ± 1.6 | 92.0 ± 1.6 | 113.9 ± 2.5 | 109.3 ± 4.3 |
| TYR | 63.7 ± 5.8 | 54.2 ± 2.6 | 69.2 ± 2.6 | 63.3 ± 6.4 | 52.8 ± 5.2 | 45.9 ± 4.6 | 62.5 ± 6.6 | 45.1 ± 5,4 | 48.5 ± 4.3 |
| TAU | 248.9 ± 32.7 | 327.7 ± 38 | 430 ± 49 | 317.8 ± 17.4 | 360.4 ± 48.7 | 295.5 ± 22.6 | 343.3 ± 31.6 | 444.9 ± 11.6 | 412.5 ± 32 |
| MET | 23.5 ± 6.7 | 52.0 ± 14 | 95.4 ± 9.1 | 33.7 ± 6.6 | 14.2 ± 3.7 | 32.4 ± 4.8 | 35.0 ± 13.2 | 22.8 ± 6.5 | 43.3 ± 3.7 |
| THR | 253.5 ± 29.4 | 239.7 ± 15.6 | 347.1 ± 31.3 | 227.7 ± 38.8 | 254.9 ± 34.4 | 274.4 ± 10.7 | 208.4 ± 8.2 | 185.7 ± 9.9 | 204.1 ± 18 |
| PHE | 45.3 ± 3.4 | 94.6 ± 2.1 | 103.1 ± 4.5 | 43.1 ± 2.5 | 63.5 ± 7.3 | 73.8 ± 4.9 | 37.2 ± 1.3 | 58.0 ± 3.9 | 72.9 ± 6.7 |
| VAL | 137.6 ± 17.3 | 304.1 ± 26.4 | 391.5 ± 21.3 | 128.2 ± 8.2 | 446.7 ± 42.6 | 636.8 ± 24.4 | 155.1 ± 11.3 | 513.1 ± 16.7 | 805.1 ± 16. |
| ILE | 49.6 ± 6.7 | 137.2 ± 16.8 | 175.6 ± 8.9 | 43.2 ± 4.2 | 177.0 ± 15.4 | 257.2 ± 9.7 | 57.1 ± 3.3 | 211.7 ± 8.6 | 325.9 ± 10. |
| LEU | 100.5 ± 15.4 | 196.2 ± 24.6 | 263.4 ± 16.7 | 95.1 ± 7.1 | 280.6 ± 21.6 | 420.4 ± 15.9 | 121.5 ± 1.6 | 341.2 ± 13.7 | 524.8 ± 19. |
| TOTAL BCAA | 24.1 ± 38.4 | 637.0 ± 67 | 830.0 ± 45 | 266.4 ± 15.9 | 904.4 ± 68.8 | 1314.4 ± 42.3 | 333.7 ± 12.2 | 1066.0 ± 31.2 | 1638.5 ± 49.6 |
| TOTAL NITROGEN | 4.71± .31 | 5.08± .17 | 6.31± .19 | 4.93± .28 | 5.07± .21 | 5.92± .18 | 4.76± .26 | 5.37± .10 | 6.03± .01 |

TABLE VIII

SKELETAL MUSCLE AMINO ACID PROFILE
(MMOL/L. MEAN ± SEM)

| | | | 11% DCAA | | | |
|---|---|---|---|---|---|---|
| | SALINE | | GLN | | NEAA | |
| | PRE | POST | PRE | POST | PRE | POST |
| GLN | 21.48 ± 3.21 | 15.96 ± 3.80 | 19.85 ± 3.17 | 21.78 ± 2.01 | 30.25± 1.63 | 21.04± 1.92 |
| ALA | 5.35 ± .55 | 558 ± .88 | 4.81 ± .44 | 5.62 ± .39 | 5.59± .23 | 8.11± 2.35 |
| GLY | 2.85 ± .31 | 2.28 ± .51 | 4.30 ± .65 | 3.22 ± .42 | 3.67± .37 | 3.63± .25 |
| ARG | 1.17 ± .24 | 0.73 ± .08 | 0.91 ± .21 | 0.78 ± .03 | 1.45± .41 | 2.06± .51 |
| SER | 1.42 ± .16 | 1.10 ± .19 | 1.42 ± .26 | 1.65 ± .13 | 1.52± .09 | 2.33± .22 |
| ASP | 0.93 ± .20 | 1.04 ± .13 | 0.50 ± .19 | 0.80 ± .21 | 1.63± .16 | 1.95± .41 |
| ASN | 0.43 ± .05 | 0.50 ± .07 | 0.51 ± .07 | 0.67 ± .08 | 0.53± .04 | 0.43± .06 |
| GLU | 6.30 ± .86 | 3.91 ± .30 | 4.48 ± .98 | 4.38 ± .84 | 11.23± .75 | 9.08± 1.25 |
| HIS | 0.81 .28 | 0.39 ± .02 | 0.45 ± .12 | 0.59 ± .11 | 0.69± .01 | 0.96± .14 |
| TYP | 0.17 ± .02 | 0.13 ± .02 | 0.27 ± .09 | 0.24 ± .05 | 0.36± .20 | 0.36± .09 |
| MET | 0.06 ± .03 | 0.04 ± .02 | 0.30 ± .02 | 0.06 ± .04 | 0.07± .01 | 0.13± .01 |
| TYR | 1.20 ± .23 | 1.11 ± .17 | 1.36 ± .30 | 1.62 ± .18 | 2.24± .27 | 2.23± .21 |
| PHE | 0.11 ± .02 | 0.14 ± .05 | 0.11 ± .03 | 0.17 ± .02 | 0.12± .03 | 0.16± .01 |
| VAL | 0.19 ± .01 | 0.21 ± .04 | 0.20 ± .01 | 0.37 ± .05 | 0.20± .04 | 0.32± .04 |
| ILE | 0.09 ± .003 | 0.11 ± .02 | 0.09 ± .01 | 0.17 ± .03 | 0.11± .03 | 0.17± .02 |
| LEU | .016± .01 | 0.28 ± .12 | .016± .01 | .023± .05 | 0.18± .05 | 0.21± .03 |
| TOTAL DCAA | 0.44 ± .02 | 0.59 ± .17 | 0.42 ± .02 | 0.77 ± .13 | 0.50± .12 | 0.69± .16 |
| TOTAL NITROGEN | 69.8 ± 8.5 | 52.8 ± 8.4 | 63.5 ± 7.0 | 68.3 ± 4.4 | 96.4 ± 5.2 | 82.8 ± 5.9 |

| | | | 44% BCAA | | | |
|---|---|---|---|---|---|---|
| | 22% BCAA | | GLN | | NEAA | |
| | PRE | POST | PRE | POST | PRE | POST |
| GLN | 18.69 ± 3.74 | 18.15 ± 3.76 | 24.83 ± 2.72 | 26.20 ± 3.86 | 22.55± 2.57 | 21.66± 2.27 |
| ALA | 4.71 ± .46 | 4.69 ± .79 | 3.16 ± .95 | 7.55 ± .89 | 4.45± .27 | 4.01± 1.67 |
| GLY | 4.06 ± .74 | 4.52 ± 1.15 | 3.70 ± .31 | 2.87 ± .17 | 4.08± .63 | 2.33± .82 |
| ARG | 1.21 ± .14 | 1. 14± .15 | 1.06 ± .20 | 0.59 ± .13 | 1.10± .39 | 0.95± .35 |
| SER | 2.10 ± .60 | 1.38 ± .22 | 1.69 ± .12 | 1.63 ± .21 | 1.72± .32 | 1.34± .57 |
| ASP | 0.85. ± .52 | 0.62 ± .15 | 1.15 ± .12 | 2.86 ± .34 | 1.29± .31 | 1.69± .76 |
| ASN | 0.43 ± .09 | 0.45 ± .08 | 0.86 ± .15 | 0.60 ± .18 | 0.42± .09 | 0.36± .09 |
| GLU | 5.96 ± .83 | 4.97 ± 1.30 | 10.29 ± .83 | 9.29 ± 1.03 | 9.00± 2.08 | 8.98± 1.98 |
| HIS | 0.79 ± .18 | 0.50 ± .03 | 0.79 ± .14 | 0.62 ± .08 | 0.71± .18 | 0.46± .23 |
| TYR | 0.32 ± .09 | 0.27 ± .05 | 0.33 ± .11 | 0.22 ± .10 | 0.29± .11 | 0.15± .04 |
| MET | 0.04 ± .03 | 0.06 ± .04 | 0.08 ± .01 | 0.12 ± .01 | 0.06± .01 | 0.09± .01 |
| THR | 1.59 ± .23 | 1.70 ± .26 | 2.57 ± .48 | 2.29 ± .42 | 1.98± .30 | 1.43± .09 |
| PHE | 0.09 ± .02 | 0.14 ± .02 | 0.13 ± .02 | 0.16 ± .01 | 0.10± .01 | 0.15± .01 |
| VAL | 0.22 ± | 0.37 ± | 0.21 ± | 0.80 ± | 0.22± | 1.01± |

TABLE VIII-continued

SKELETAL MUSCLE AMINO ACID PROFILE (MMOL/L. MEAN ± SEM)

| | | | | | | |
|---|---|---|---|---|---|---|
| | .03 | .07 | .03 | .04 | .01 | .06 |
| ILE | 0.10± | 0.17± | 0.11± | 0.27± | 0.10 ± | 0.29± |
| | .02 | .03 | .02 | .03 | .003 | .02 |
| LEU | 0.16± | 0.26± | 0.17± | 0.42± | 0.17 ± | 0.44± |
| | .02 | .04 | .02 | .05 | .001 | .01 |
| TOTAL | 0.47± | 0.80± | 0.49± | 1.49± | 0.48 ± | 1.75± |
| BCAA | .07 | .14 | .07 | .11 | .01 | .07 |
| TOTAL | 65.2 ± | 62.5 ± | 83.6 ± | 85.9 ± | 75.9 ± | 70.8 ± |
| NITROGEN | 10.3 | 9.6 | 7.0 | 8.9 | 11.8 | 8.4 |

TABLE VIII

SKELETAL MUSCLE AMINO ACID PROFILE (MMOL/L. MEAN ± SEM)

| | | | 11% BCAA | | | |
|---|---|---|---|---|---|---|
| | SALINE | | GLN | | NEAA | |
| | 6° | 24° | 6° | 24° | 6° | 24° |
| GLN | −2.69± | −1.71± | −1.19± | −0.16± | −2.10± | −1.92± |
| | 1.07 | .70 | .46 | .82 | .62 | 1.72 |
| ALA | −2.19± | −0.72± | −0.92± | −0.73± | −1.09± | −0.95± |
| | .52 | 1.26 | .23 | .44 | .28 | .25 |
| GLY | −1.38± | −0.56± | −0.66± | −0.28± | −0.86± | +0.47± |
| | .36 | 1.05 | .20 | .31 | .19 | .72 |
| ARG | −0.83± | +0.12± | −0.29± | −0.09± | −0.13± | +0.28± |
| | .14 | .72 | .13 | .25 | .07 | .18 |
| SER | −0.49± | +0.09± | −0.11± | +0.11± | −0.14± | +0.37± |
| | .11 | .49 | .28 | .23 | .07 | .29 |
| ASP | +0.04± | +0.19± | −0.01± | +0.02± | −0.00± | −0.03± |
| | .04 | .12 | .01 | .05 | .01 | .11 |
| ASN | −0.22± | −0.14± | −0.07± | −0.14± | −0.11± | −0.38± |
| | 0.9 | .11 | .04 | .04 | .04 | .29 |
| GLU | +0.10± | +0.21± | +0.06± | +0.08± | +0.06± | +0.17± |
| | .18 | .11 | .07 | .02 | .07 | .09 |
| HIS | −.44± | −0.19± | −0.09± | +0.08± | −0.03± | −0.05± |
| | .09 | .44 | .17 | .20 | .14 | .19 |
| TYR | −0.26± | −0.08± | −0.13± | −0.11± | −0.13± | −0.04± |
| | .09 | .40 | .02 | .04 | .04 | .08 |
| TAU | −1.05± | +0.78± | −0.23± | +0.18± | −0.27± | +1.39± |
| | .33 | 2.18 | .28 | .51 | .10 | .74 |
| MET | −0.32± | −0.33± | −0.23± | −0.59± | −0.61± | −2.13± |
| | .09 | .33 | .11 | .28 | .40 | 1.08 |
| THR | −1.06± | +0.72± | −0.30± | −0.27± | −0.07± | +1.28± |
| | .10 | .86 | .13 | .32 | .43 | .67 |
| PHE | −0.37± | −0.20± | −0.12± | −0.19 | −0.13± | −0.12± |
| | 0.5 | .36 | .04 | .08 | .03 | .03 |
| VAL | −0.46± | +0.33± | +0.14± | +0.02± | +0.31± | +0.49± |
| | .17 | .68 | .08 | .11 | .26 | .23 |
| ILE | −0.24± | +0.12± | +0.08± | +0.06± | +0.27± | +0.42± |
| | .03 | .30 | .02 | .08 | .19 | .15 |
| LEU | −0.43± | +0.04± | +0.06± | −0.08± | +0.30± | +0.50± |
| | .09 | .54 | .07 | .08 | .25 | .24 |
| TOTAL | −1.14± | +0.49± | +0.28± | −0.03± | −0.88± | +1.40± |
| BCAA | .26 | 1.51 | .14 | .19 | .57 | .50 |
| TOTAL | −19.05± | −3.59± | −6.52± | −3.25± | −7.39± | −1.90± |
| NITROGEN | 4.06 | 12.1 | 1.81 | 3.07 | .52 | 6.40 |

| | | | 44% BCAA | | | |
|---|---|---|---|---|---|---|
| | 22% BCAA | | GLN | | NEAA | |
| | 6° | 24° | 6° | 24° | 6° | 24° |
| GLN | −1.92± | −1.24± | −0.73± | +0.74± | −2.00± | −4.13± |
| | .60 | .44 | .60 | 1.76 | .32 | 1.45 |
| ALA | −0.98± | −2.55± | −0.97± | −1.99± | −1.17± | −1.49± |
| | .84 | .84 | .22 | .98 | .09 | .67 |
| GLY | +0.05± | −0.89± | −0.44± | −0.78± | −0.39± | −0.25± |
| | .40 | .53 | .14 | .39 | .21 | .25 |
| ARG | +0.28± | −0.26± | −0.11± | −0.28± | −0.13± | +0.02± |
| | .38 | .22 | .24 | .24 | 0.06 | .16 |
| SER | +.05± | +0.65± | −0.14± | −0.13± | −0.22± | +0.16± |

TABLE VIII-continued

| SKELETAL MUSCLE AMINO ACID PROFILE (MMOL/L. MEAN ± SEM) | | | | | | |
|---|---|---|---|---|---|---|
| | .45 | .30 | .10 | .22 | .11 | .06 |
| ASP | +0.02± | +0.00± | +0.03± | −0.24± | +0.01± | −0.09± |
| | .04 | .08 | .03 | .21 | .03 | .11 |
| ASN | −0.15± | −0.12± | −0.07± | −0.32± | −0.08± | −0.12± |
| | .09 | .13 | .05 | .13 | .05 | .05 |
| GLU | +0.11± | +0.23± | +0.16± | +0.21± | −0.01± | −0.10± |
| | .06 | .13 | .04 | .15 | .03 | .09 |
| HIS | −0.34± | −0.24± | −0.03± | −0.25± | −0.06± | −0.03± |
| | .27 | .36 | .10 | .22 | .12 | .01 |
| TYR | −0.19± | −0.14± | −0.10± | −0.18± | −0.07± | −0.06± |
| | .06 | .05 | .01 | .09 | .03 | 0 |
| TAU | −0.08± | +0.24± | −0.08± | −0.48± | +0.21± | −0.50± |
| | .61 | .39 | .15 | .34 | .07 | .1 |
| MET | −0.74± | −1.66± | −0.21± | −1.69± | −0.26± | −0.56± |
| | .41 | .86 | .06 | .35 | .16 | .21 |
| THR | +0.19± | −0.13± | −0.06± | +0.57± | +0.28± | +0.27± |
| | .37 | .46 | .11 | .35 | .17 | .1 |
| PHE | −0.14± | −0.13± | −0.14± | −0.27± | −0.07± | −0.16± |
| | .09 | .15 | .08 | .15 | .03 | .12 |
| VAL | +0.62± | +1.12± | +0.67± | +0.37± | +1.34± | +1.26± |
| | .46 | 1.01 | .23 | .45 | .17 | .65 |
| ILE | +0.49± | +0.39± | +0.42± | +0.51± | +.80± | +0.97± |
| | .21 | .15 | .04 | .21 | .07 | .48 |
| LEU | +0.51± | +0.57± | +0.61± | +0.69± | +1.14± | +1.44± |
| | .33 | .39 | .06 | .33 | .13 | .69 |
| TOTAL | +1.64± | +2.09± | +1.71± | +1.57± | +3.28± | +3.67± |
| BCAA | .86 | 1.54 | .22 | .83 | .19 | 1.43 |
| TOTAL | −7.70± | −8.42± | −2.50± | −7.40± | −3.27± | −7.60± |
| NITROGEN | 5.90 | 1.90 | 2.50 | 8.70 | 1.62 | 2.91 |

EXAMPLE 6

The Effects of Glutamine Enriched Oral Diet on Small Bowel After Intestinal Resection

Introduction

Compensatory growth of the small intestine after partial resection involves all coats of the bowel wall, but is dominated by villus hyperplasia. Increased villous height and crypt depth are accompanied by dilation and lengthening of the intestinal remnant, Williamson, R. C. N., "Intestinal adaption," N. Engl. J. Med., 298:1393–1444 (1978). Small bowel resection is followed by adaptive morphological and functional changes. Oral intake has been proved to be an important stimulus in the regulation of mucosal hyperplasia after intestinal resection, Levine, G. M., et al., "Small-bowel resection, oral intake is the stimulus for hyperplasia," Dig. Dis. 21:542–545 (1976). Luminal nutrients are important in maintaining normal mucosal growth and if oral intake is not maintained after resection of small bowel, the residual bowel loses its weight and becomes hypoplasic. Patients with short bowel after small bowel resection are supported by parenteral nutrition; their survival depends on the capacity of the residual intestinal system to adapt. The use of elemental diets and parenteral nutrition allows sufficient time for the development of intestinal adaptation and a slow return to complete oral intake, Weser, E., "The management of patients after small bowel resection," Gastroenterology 71:146–150 (1976).

Glutamine is an important fuel for enterocytes, and its utilization by the intestine appears to increase after surgical stress, Souba, W. W., et al., "Postoperative alteration of arteriovenous exchange of amino acids across the gastrointestinal tract," Surgery 94(2):342 (1983). Glutamine could serve as a local trophic factor, promoting mucosal growth when intestinal hypoplasia develops. This study investigated whether addition of glutamine to an elemental diet was associated with any advantage in terms of adaptation and recovery by the small intestine after subtotal resection. The study was designed to feed rats with a glutamine enriched elemental diet after a two-thirds small bowel resection. The mucosal adaptation of residual bowel was compared with controlled diet and sham-operated groups.

Materials and Methods

Male wistar rats, weighing 175–200 gm, were purchased from the Charles River Breeding Laboratories, Inc., and allowed to acclimatize for 5 days. The rats were provided free access to water and fed with Purina chow diet. They were kept in individual cages and weighed every other day. After acclimatization, the rats with normal weight gain were randomly divided into four groups.

On the first day of study, the rats were anesthnetized with intraperitoneal injection of pentobarbital (50 mg/kg). The abdomen was opened via a midline incision, the whole length of small intestine from the ligament of Treitz to the ileocaecal valve was exteriorized and measured twice without stretch by a long black thread. The mean of the two measurements was determined. Then two-thirds resection of the small intestine beginning 5 cm distal to the ligament of Treitz was performed by the method of Lambert, R., "Surgery of the digestive system of the rats," Charles C. Thomas, Springfield, Ill., pp32–35, 413–416 (1965). The resection margins were anastomosed end to end with 6–0 prolene. The intestine was replaced in the abdominal cavity and the abdominal wall was closed with 2–0 prolene. Control group was sham operated, undergoing transection and reanastomosis of the small intestine at the distal site, two-thirds of total length measured beginning 5 cm distal to the ligament of Treitz. The rats were kept in individual cages after operation and allowed to sip water on the first postoperative day.

Oral feeding was started from the second postoperative day. Rats in group 1 were orally alimented with glutamine enriched elemental diet (4.18%), and rats in group II were alimented with glycine enriched elemental diet (4.18%). Rats in group III (resected rats) and rats in group IV (sham-operated rats) were fed with ordinary chow diet. The feeding was continued for 7 days and their daily body weights were recorded until the day of harvest.

Preparation of Glutamine and Glycine Elemental Diets

The elemental diet ($NBC_0$ Biochemicals, Inc., Cleveland, Ohio) contains 0.2% Choline chloride, 10% Corn oil, 46.9% Dextrin-white, 23.4% Surcose, 5% Salt mixture, 0.5% Vitamin mixture and 9.82% of 17 kinds essential and nonessential amino acids. Glutamine or glycine powder was added to the elemental diet to make 41.8% of glutamine or glycine enriched elemental diet, i.e. 28% of the total amino acids.

Harvest Procedures

After 7 days of feeding, the rats were sacrificed. They were anesthetized with intraperitoneal injection of pentobarbital (50 mg/kg). The abdomen was opened and the incision extended to the chest cavity. Five ml of blood was drawn by puncture of the right ventricle for determination of blood ammonia and plasma glutamine levels. The intestine was harvested immediately following blood withdrawal. The entire small intestine was removed with careful separation of the mesentery, keeping close to the intestinal serosal. The removed intestine was suspended under fixed tension of 4.5 gm and 9 points were marked. For the rats with bowl resection, points of 5, 10 and 12.5 cm proximal to the anastmosis which represented the proximal jejunum and distal duodenum, and points of 2,5 and 10 cm distal to the anastomosis which represented the residual proximal ileum close to the anastomosis, and points of 5, 10 and 15 cm proximal to the ileocaecal valve which represented the residual distal ileum, were marked with straight pins passed through the bowel. The six intestinal segments were separated. For the rats in sham-operated group, the proximal two segments were marked from 1 cm distal to the ligament of Treitz and measured upward. Segments 1a, 2a and 3a were rinsed in chilled saline and embedded in 10% buffered formaline for 4 hours, then transferred into 70% ethanol for fixation. Segments 1b, 2b and 3b were rinsed in chilled saline, their lumens were opened and were weighed wet weight. The intestinal segments were transferred into 5 ml of chilled saline and minced with sharp scissors. A homogenate was prepared, using two fifteen second periods on a Polytron homogenizer (Brinkman Instruments, Westbury, N.Y.), followed by sonication with a sonicator (Heat system Laboratories, Plainview, N.Y.) at a power setting of 2, for thirty seconds. Saline homogenates for DNA and protein analysis were stored at −30° C.

Analytic Methods

The intestinal homogenates were analyzed for total protein according to the method of Lowry, O. H. et al, "Protein measurement with the Folin phenol reagent," J. Biochem., 193:265–275 (1951). DNA was determined according to the method of Burton, K., "A study of the conditions and mechanism of the diphenylamine reaction for the colorimetric estimation of deoxyribonucleic acid," Biochem. 62:315–323 (1965). Histologic sections were embedded in paraffin, stained with hematoxyline and eosin, and examined under a light microscope at 40× magnification. Twenty representative, tall, well-oriented complete villi were chosen to measure mucosal thickness and villous height using an eyepiece micrometer, and an average value obtained. The villus number was counted with the intestine put in the central horizontal line of 40× magnified field.

Results

Figure 7:
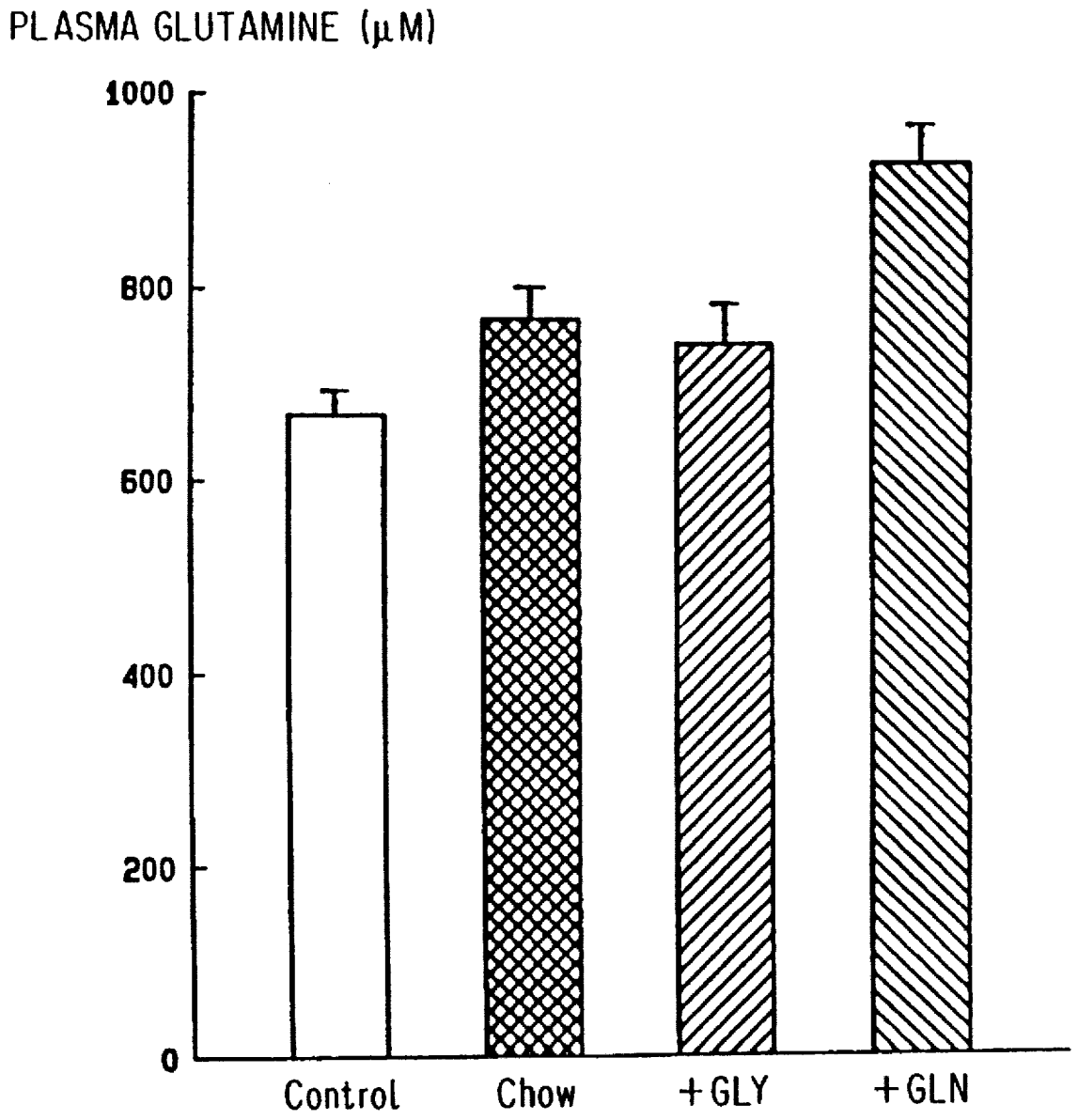
FIG. 7 is a graphic presentation of the effect of oral diet on plasma glutamine levels after subtotal small intestine resection.
Figure 8:
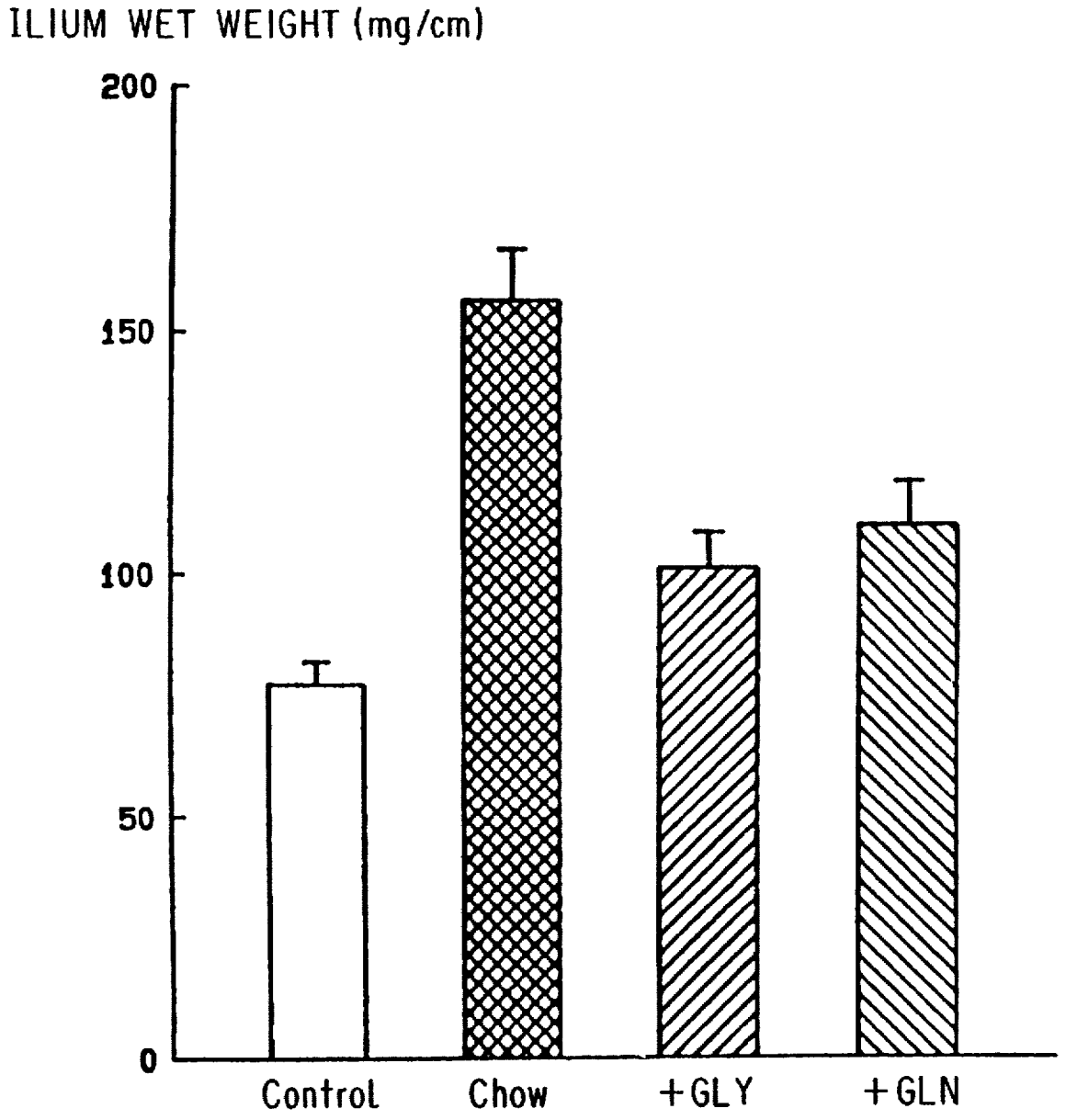
FIG. 8 is a graphic presentation of data demonstrating the effect of oral diet on distal ilium weight after subtotal small intestine resection.
Figure 9:
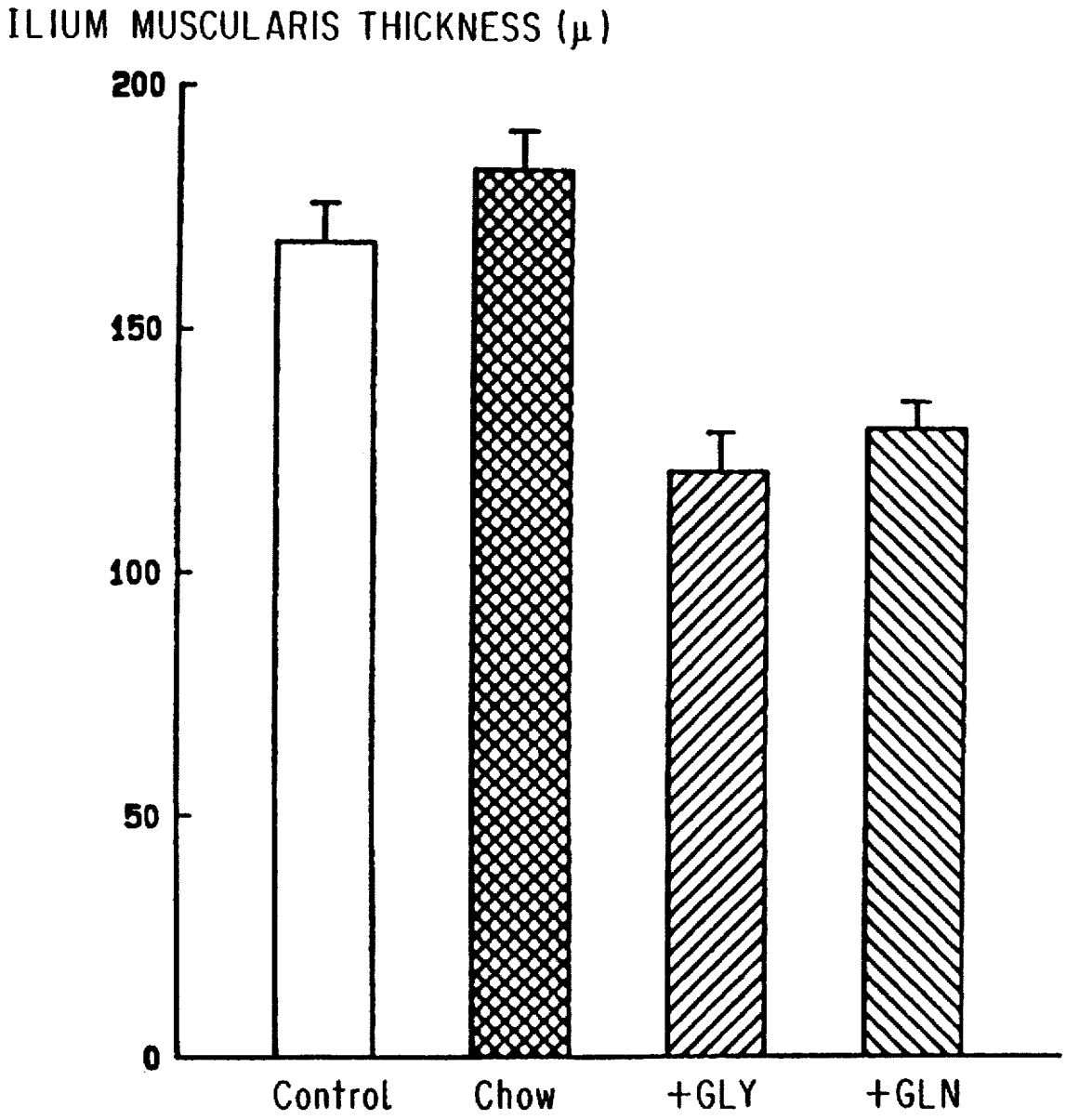
FIG. 9 is a graphic presentation of data demonstrating the effects of oral diet on muscularis thickness in distal ilium after subtotal resection of small intestine.
Figure 10:
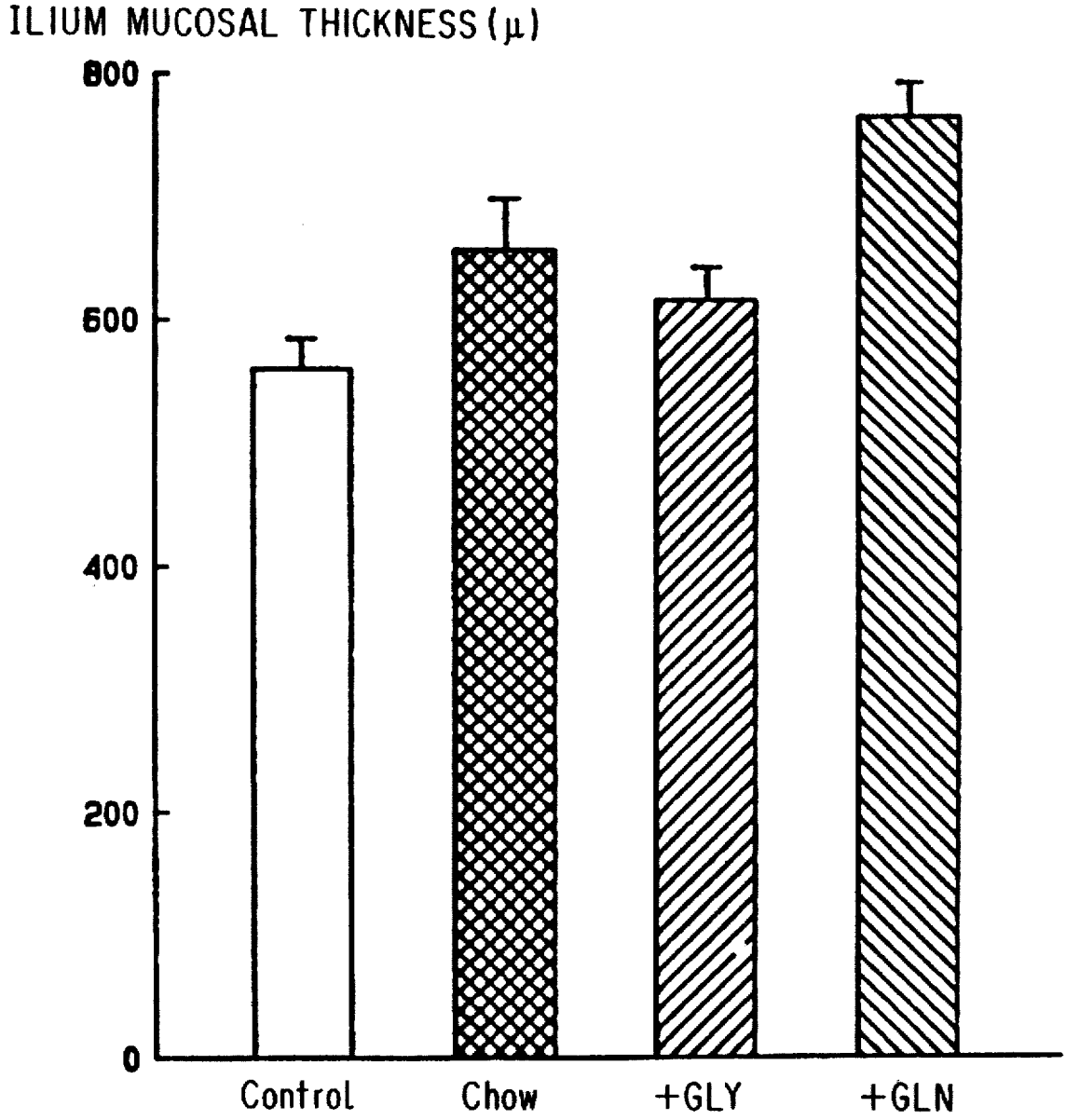
FIG. 10 is a graphic presentation of data demonstrating the effect of oral diet on mucosal thickness of distal ilium after subtotal resection of small intestine.
Figure 11:
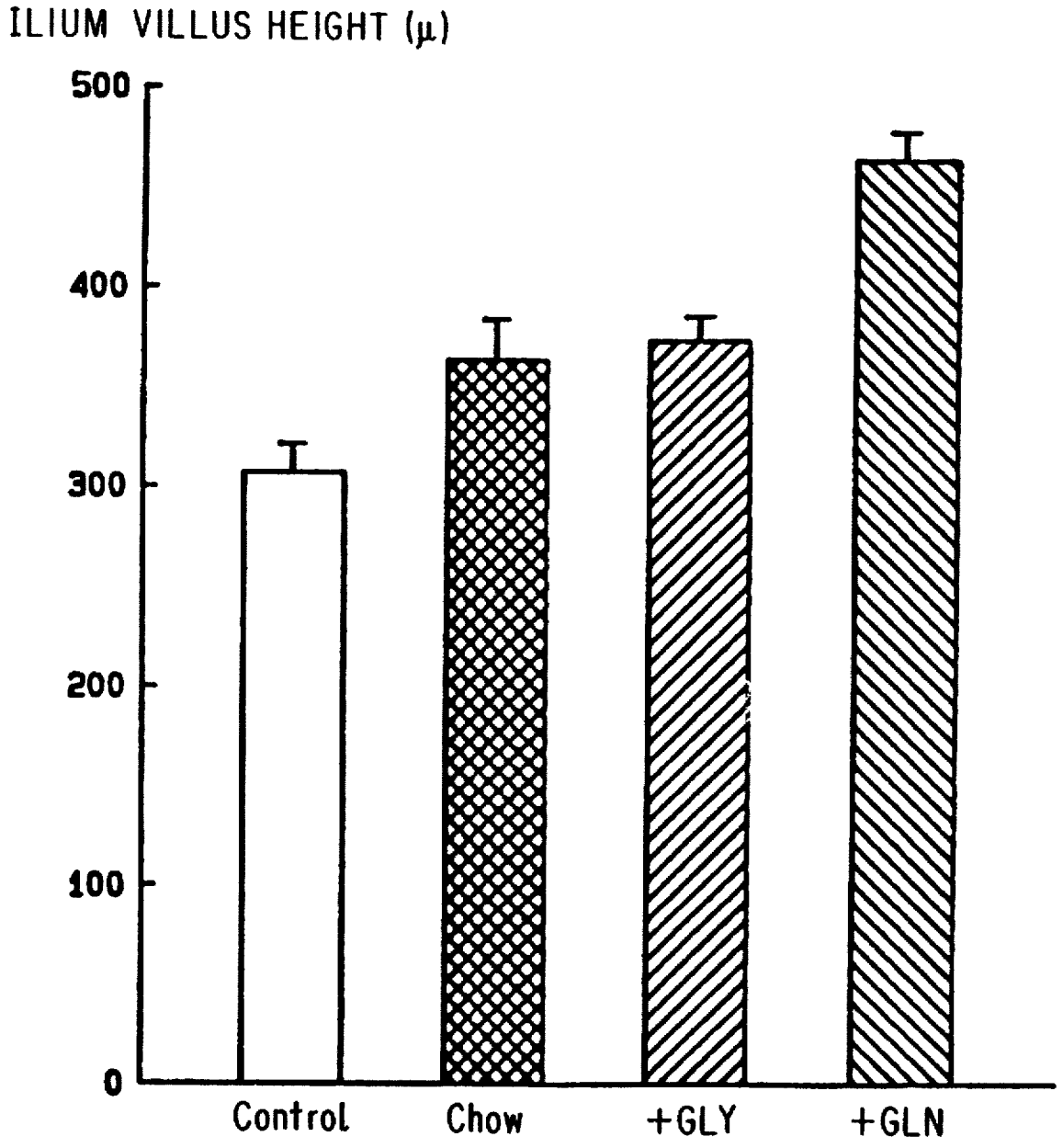
FIG. 11 is a graphic presentation of the effect of oral diet on villus height in distal ilium after subtotal resection of small intestine.

FIG. 7 demonstrates that the glutamine-supplemented diet results in higher plasma glutamine levels. Based on measurements of weight/cm (FIG. 8), there seemed to be little difference between the glutamine-supplemented (+GLN) and glutamine-free diets, with both supporting less intestinal hypertrophy than normal chow. However, on examination of intestinal mucosa with measurements of mucosal thickness (FIG. 10) and villus height (FIG. 11), the glutamine-supplemented diet proved superior.

EXAMPLE 7

Preservation of Small Bowel Mucosa Using Glutamine-Enriched Parenteral Nutrition Parenteral nutrition results in mucosal atrophy of the small intestine (Johnson, L. R. et al., Gastroenterology 68:1177–1183) (1975). This response may be related to a decrease in gastrointestinal secretions and trophic hormones and also a relative lack of specific nutrients required for enterocyte proliferation. Glutamine is a major oxidative fuel for the small intestine but is not present in standard parenteral solutions. To determine the influence of dietary glutamine the small intestinal response to the administration of parenteral solutions enriched with varying concentrations of this amino acid was evaluated.

MATERIALS AND METHODS

Conditioned male Wistar rats (n=42, wt 210–230 g) underwent jugular venous catherterization and were fitted with a swivel assembly which allows long term infusion in unrestrained animals (Burt, M. E. et al., J. Physiol. 238:H599–603 (1980). All rats were housed in individual metabolic cages and allowed access to drinking water. Control animals received 0.9% saline infusion and Purina rat chow ad libitum. Three groups of rats received intravenous nutrition. All nutrient solutions were isonitrogenous (0.9 g nitrogen/100 ml) and isocaloric (98Kcal/100 ml), and contained equal concentrations of essential amino acids, nonessential amino acids and dextrose. The nonessential amino acid component of each solution was adjusted in order to provide glutamine concentrations of 0.2 or 3 g/100 ml. parenteral solutions were infused at a rate of 48 ml/24 hrs. Urine output and nitrogen excretion were measured daily. Animals were sacrificed following 7 days of parenteral nutrition and blood was obtained for determination of glutamine and ammonia concentrations. Both full thickness jejunal segments and mucosal samples were obtained from defined sections of the intestine. All samples were weighed, and homogenates were assayed for DNA and protein. Histologic paraffin sections of 5 um thickness were prepared. Measurements of jejunal villus height, number and mucosal thickness were performed in a blinded fashion.

RESULTS AND DISCUSSION

Wet weight, DNA, protein and villus height decreased in all rats receiving intravenous nutrition when compared to orally fed controls (Table X). Plasma glutamine concentration increased following infusion of solutions containing glutamine. Jejunal mucosal weight increased significantly when compared to rats receiving glutamine free solutions. Full thickness jejunal weight did tend to increase with glutamine intake although the response was not statistically significant. Both mucosal and full thickness jejunal DNA increased following glutamine infusion at 2 and 3% concentrations. These changes were accompanied by histological evidence of mucosal growth. Villus height and mucosal thickness increased in a dose dependent manner in proportion to quantity of glutamine administered. All animals were in positive nitrogen balance but rats receiving the 2% glutaimine solution retained the greatest quantity of nitrogen throughout the study.

The provisions of glutamine in parenteral solutions results in an increase in jejunal mucosal weight, DNA content and vilus height when animals are maintained on intravenous nutrition. An increase in the mucosal mass of the small intestine may improve small bowel function and facilitate the introduction of enteral nutrition. Glutamine may be a nutrient necessary for mucosal support which is not present in standard parenteral solutions at the present time.

TABLE X

| | 0 GLN (n = 10) | 2% GLN (n = 11) | 3% GLN (n = 10) | CHOW (n = 11) |
|---|---|---|---|---|
| PLASMA GLN (umol/L) | 890.3 ± 42.4 | 1105.8 ± 98.8* | 717.1 ± 46 | |
| FULL THICKNESS WT (mg/cm) | 30.6 ± 0.8 | 31.4 ± 1.0 | 32. ± 0.6 | 46.6 ± 3.6 |
| MUCOSAL WT (mg/cm) | 17.7 ± 0.7 | 20.4 ± 1.1** | 20.3 ± 1.0** | 29.3 ± 2.3 |
| JEJUNAL DNA (ug/cm) | 252.8 ± 9.3 | 279.9 ± 7.3** | 303.1 35 19.4* | 370.2 ± 33.0 |
| MUCOSAL DNA (ug/cm) | 101.7 ± 5.9 | 134.0 ± 7.1*** | 125.1 ± 7.6** | 171.0 ± 12.7 |
| VILLUS HT | 266.5 ± 8.4 | 294.0 ± 7.9** | 306.4 ± 9.9*** | 405.6 ± 17.3 |
| MUCOSAL THICKNESS (um) | 422.6 ± 9.7 | 448.1 ± 8.9* | 452.6 ± 11.5* | 589.6 ± 20.9 |

*p < 0.05, p < 0.025, *p < 0.005 vs 0 GLN
GLN = glutamine

EXAMPLE 8

Effect of Glutamine - Enriched Parenteral Nutrition Following Treatment With 5-Fluorouricil Addition of the amino acid glutamine (GLN) to nutrient solutions significantly enhances bowel cellularity during parenteral feeding. To evaluate the effect of GLN on mucosal regeneration following injury, 5 fluorouricil (5FU) was administered to rats receiving parenteral nutrition (PN). Following jugular venous catherization male Wistar rats (n=40, wt 200–230 g) received a continuous infusion of isonitrogenous isocaloric solutions with (+) or without (–) GLN.5FU was administered in increasing doses (0,100,150 mg/kg i/p) to 24 animals at the initiation of PN (short-term) and to a further 16 animals (150 mg/kg) who had received PN for 5 days prior to treatment (long-term). At harvest, 4 days following 5FU, WBC, Hb, platlets and plasma GLN were measured, jejunal samples were weighed, assayed for DNA and protein and histologic sections were prepared. A portion of the results are shown (mean ± SEM, *p<0.05, **p<0.025 compared to –GLN).

| | SHORT-TERM PARENTERAL NUTRITION | | | | LONG-TERM PN | |
|---|---|---|---|---|---|---|
| | 0 mg/kg 5 FU | | 150 mg/kg 5 FU | | 150 mg/kg 5 FU | |
| | –GLN | +GLN | –GLN | +GLN | –GLN | +GLN |
| Survival | 100% | 100% | 85% | 85% | 25% | 75% |
| Mucosal Wt mg/cm | 22.6 ± 1.1 | 29 ± 1.8* | 15.6 ± 1.4 | 22.7 ± 3.1 | 10.7 ± 1.0 | 15 ± 1.0** |
| Mucosal DNA ug/cm | 151.7 ± 7.4 | 188 ± 13.5* | 79.9 ± 6.7 | 113.7 ± 19/7* | 59.2 ± 8.3 | 72.7 ± 5.2 |
| Muc Protein | 2.56 ± 0.1 | 2.94 ± 0.18 | 1.3 ± 0.06 | 1.96 ± 0.3** | 0.75 ± 0.3 | 1.11 ± 0.1 |

5FU treatment diminished intestinal weight, DNA and protein. Rats receiving GLN had significantly greater mucosal mass when compared to animals receiving standard solution. Addition of GLN was associated with increased survival in long-term animals. The provision of GLN in nutrient solutions improves small bowel cellularity and modifies the gastrointestinal toxicity of 5FU. Such therapy may diminish morbidity and mortality in patients whose gastrointestinal barrier defences are impaired.

Having now fully described the invention, it will now become readily apparent to one skilled in the art that many changes and modifications may be made thereto without affecting the spirit or scope thereof.

What is claimed as new and is desired to be covered by Letters Patent is:

[1. A method of treating catabolic dysfunction in an animal, which comprises administering to said animal a therapeutically effective amount of glutamine or an analogue thereof in an amount greater than that present in the normal diet of said animal.]

[2. The method of claim 1 wherein said catabolic dysfunction is enteral or parenteral.]

[3. The method of claim 2 wherein said enteral dysfunction occurs substantially associated with intravenous feeding.]

[4. The method of claim 3 wherein said enteral dysfunction affects the small intestine.]

[5. The method of claim 2 wherein said parental dysfunction occurs substantially associated with physical trauma.]

[6. The method of claim 5 wherein said physical trauma is associated with surgery, sepsis, burn injuries, anorexia, chemotherapy, radiation therapy, or uncontrolled diabetes.]

[7. The method of claim 1 wherein said administration of a therapeutically effective amount of glutamine is enteral or parenteral.]

[8. The method of claim 7 wherein said administration is by use of a dietary supplement.]

[9. The method of claim 7 wherein said parenteral administration is by subcutaneous, intramuscular, or intravenous injection, nasopharyngeal or mucosal absorption, or transdermal absorption.]

[10. The method of claim 8 wherein said enteral administration is at the rate of 0.3 to 2.0 grams of glutamine or glutamine analogue per kilogram of body weight per day.]

[11. The method of claim 10 wherein said enteral administration is at the rate of 0.3 to 1.5 grams of glutamine or glutamine analogue per kilogram of body weight per day.]

[12. The method of claim 11 wherein said enteral administration is at the rate of 0.4 to 1.0 grams of glutamine or glutamine analogue per kilogram of body weight per day.]

[13. The method of claim 9 wherein said parenteral administration is at the rate from 0.2 to 3.0 grams of glutamine or glutamine analogue per kilogram of body weight per day.]

[14. The method of claim 13 wherein said parenteral administration is at the rate from 0.3 to 2.5 grams of glutamine or glutamine analogue per kilogram of body weight per day.]

[15. The method of claim 14 wherein said parenteral administration is at the rate from 0.4 to 2.0 grams of glutamine or glutamine analogue per kilogram of body weight per day.]

[16. A composition comprising a glutamine-rich composition for preventing or ameliorating a catabolic dysfunction.]

[17. A container for a liquid composition adapted for intravenous administration of said composition, comprising a receptacle for said composition, and liquid conducive means connected to said receptacle capable of attachment to a needle for intravenous dispensation, wherein said composition comprises an amount of glutamine capable of inhibiting a catabolic dysfunction in an animal.]

[18. The container of claim 17 wherein said catabolic dysfunction is associated with skeletal muscle wasting.]

*19. The method of treating atrophy of skeletal muscle, intestinal mucosa, or both in an animal, which comprises enterally administering to said animal a therapeutically effective amount of glutamine or a functional analogue thereof which retains the characteristics of glutamine in an amount greater than that present in the normal diet of said animal wherein said therapeutically effective amount of glutamine or a functional derivative thereof is 0.4–3.0 g/kg/day.*

*20. The method of claim 19 which comprises inhibiting atrophy of intestinal mucosa.*

*21. The method of claim 20 wherein said atrophy of intestinal mucosa occurs substantially associated with intravenous feeding.*

*22. The method of claim 19 which comprises inhibiting atrophy of skeletal muscle.*

*23. The method of claim 22 wherein said atrophy of skeletal muscle occurs substantially associated with physical trauma.*

*24. The method of claim 23 wherein said physical trauma is associated with surgery, sepsis, burn injuries, anorexia, chemotherapy, radiation therapy, or uncontrolled diabetes.*

*25. The method of claim 19 wherein said administration is by use of a dietary supplement.*

*26. The method of claim 19 wherein said enteral administration is at the rate of 0.4 to 2.0 grams of glutamine or glutamine analogue per kilogram of body weight per day.*

*27. The method of claim 26 wherein said enteral administration is at the rate of 0.4 to 1.5 grams of glutamine or glutamine analogue per kilogram of body weight per day.*

*28. A method according to claim 26, wherein said enteral administration is at the rate of 0.4 to 1.0 grams of glutamine or glutamine analogue per kilogram of body weight per day.*

* * * * *